(12) United States Patent
Allen et al.

(10) Patent No.: US 9,868,959 B2
(45) Date of Patent: Jan. 16, 2018

(54) ENGINEERED MICROALGAE WITH ENHANCED LIPID PRODUCTION

(75) Inventors: Andrew Allen, San Diego, CA (US); Christopher Lee Dupont, San Diego, CA (US)

(73) Assignee: J. Craig Venter Institute, Rockville, MD (US)

( * ) Notice: Subject to any disclaimer, the term of this patent is extended or adjusted under 35 U.S.C. 154(b) by 0 days.

(21) Appl. No.: 13/993,859

(22) PCT Filed: Dec. 13, 2011

(86) PCT No.: PCT/US2011/064627
§ 371 (c)(1),
(2), (4) Date: Feb. 13, 2014

(87) PCT Pub. No.: WO2012/082731
PCT Pub. Date: Jun. 21, 2012

(65) Prior Publication Data
US 2014/0162330 A1    Jun. 12, 2014

Related U.S. Application Data

(60) Provisional application No. 61/422,462, filed on Dec. 13, 2010.

(51) Int. Cl.
*C12P 7/64* (2006.01)
*C12N 15/52* (2006.01)
*C12N 15/74* (2006.01)
*C12N 15/82* (2006.01)

(52) U.S. Cl.
CPC ......... *C12N 15/8247* (2013.01); *C12N 15/52* (2013.01); *C12N 15/74* (2013.01); *C12P 7/6463* (2013.01)

(58) Field of Classification Search
CPC combination set(s) only.
See application file for complete search history.

(56) References Cited

U.S. PATENT DOCUMENTS 6,027,900 A  * 2/2000 Allnutt et al. ............. 435/6.15
2009/0087890 A1* 4/2009 Pyle et al. ................. 435/167

FOREIGN PATENT DOCUMENTS

WO    WO 2010132413 A1 * 11/2010 ............... C12P 7/64

OTHER PUBLICATIONS

Leon-Banares et al (Transgenic microalgae as green cell-factories, Trends in Biotechnology vol. 22 No. 1 Jan. 2004.*

* cited by examiner

*Primary Examiner* — Kagnew H Gebreyesus
(74) *Attorney, Agent, or Firm* — Foley Hoag LLP

(57) ABSTRACT

Described herein are engineered microalgae that exhibit enhanced lipid production during exponential growth. Such engineered microalgae are useful, for example, for the production of biofuels.

10 Claims, 13 Drawing Sheets

Figure 2 *Phaeodactylum tricornutum* Nitrate Reductase

A (SEQ ID NO: 1)
MVPKPEDPTVKAENNAAMDQLSLLDKDDISSASRSCRELYGPYPKAIPVPFLNSRNEAREGDTPAASVIAQAK
TIFDVPADYRDVGTPDEWVPRDGRLVRLTGKHPFNVEPPLAILKQHRFITPSSLHYVRNHGACPKLSWKEHTV
CVGGKLVPNALELSMDEIVAMEPRELPVTLVCAGNRRKEQNMIRQTIGFNWGPSGVSTSVWKGVLLRDLLLRA
GVSEKNMAGKHVEFIGVEDLPNKVGPGPFQEEPWGKLVKYGTSVPLARAMNPAYDILIAYEQNGEVLQPDHGY
PVRLIIPGYIGGRMIKWLKYINVIPHETKNHYHYHDNRILPGGWWYKPEYIFNELNINSAIAAPDHNETLSIA
KNIAKTYDVTGYAYTGGGRLITRVEISVDGGIHWELAKLERKEQPTDYGMYWCWTWWNYEVKVADLVGAKEII
CRAWDESNNPQPVVPTWNLMGMGNNQAFRVKVHMDKTASGEHVFRFEHPTQPGQQTGGWMTKVATKPESAGFG
RLLEVQGESKEDAAPAPPPKENTKIFTMEEIEKHNTEEDCWIVVKDRVYDCTEYLELHPGGIDSIVINGGADS
TEDFVAIHSTKATKMLEKYYIGQLDKSSVAEEKKQEDEPLVDADGNALALNPKKKTPFRLQNKITLSRDSYLL
DFALPSPKHVLGLPTGKHMFISALINGEMVLRRYTPISSNYDIGCVKFVVKAYRPCERFPDGGKMSQYLDQIN
VGDYVDMRGPVGEFEYSANGSFTIDAEPCFATRFNMLAGGTGITPVMQIAAEILRNPQDPTQMSLIFACREEG
DLLMRSTLDEWAANFPHKFKIHYILSDSWSSDWKYSTGFVDKALFSEYLYEAGDDVYSLMCGPPIMLEKGCRP
NLESLGHKKDKIFSF

B (SEQ ID NO: 2)
ATGGTACCGAAACCTGAAGATCCCACAGTCAAGGCAGAGAATAATGCGGCGATGGATCAACTTAGTCTCCTCG
ACAAAGATGATATATCGTCGGCTTCTCGCTCGTGCCGAGAACTCTACGGACCTTACCCCAAAGCTATTCCTGT
GCCGTTCTTGAATTCTCGTAACGAAGCTCGCGAAGGTGACACTCCCGCCGCCAGCGTCATCGCGCAAGCCAAA
ACCATCTTTGACGTACCGGCCGGACTATCGTGACGTGGGAACACCGGATGAATGGGTTCCCCGCGATGGACGCC
TCGTGCGTCTGACGGGTAAGCATCCCTTCAACGTCGAACCACCGCTGGCGATTCTGAAGCAGCATCGATTTAT
TACGCCGTCCTCGTTGCATTACGTACGCAACCACGGAGCGTGCCCGAAGCTGTCTTGGAAAGAACACACTGTT
TGTGTGGGAGGAAAACTGGTACCGAATGCCTTGGAGCTCTCGATGGACGAAATCGTAGCGATGGAACCGCGAG
AGCTGCCCGTCACGTTGGTCTGTGCCGGAAATCGTCGGAAGGAACAAAACATGATCCGTCAAACAATCGGCTT
CAACTGGGGCCCGAGCGGCGTCTCAACCAGCGTTTGGAAGGGAGTGCTCCTACGCGATTTGTTGCTCCGCGCA
GGGGTTTCGGAAAAGAACATGGCAGGGAAGCACGTCGAATTTATTGGTGTCGAAGACTTGCCGAACAAGGTGG
GACCCGGGCCGTTCCAGGAGGAACCATGGGGCAAACTTGTCAAGTACGGAACCAGTGTCCCGCTCGCTCGGGC
TATGAATCCAGCGTACGACATCCTCATTGCCTATGAGCAGAACGGCGAAGTCTTGCAGCCCGATCACGGCTAC
CCCGTCCGTCTCATCATTCCTGGTTATATTGGAGGACGGATGATTAAATGGCTTAAATACATCAACGTGATTC
CGCACGAAACCAAGAATCACTATCATTACCACGACAATCGCATTTTACCGGGAGGTTGGTGGTACAAACCGGA
GTACATTTTCAATGAACTCAACATCAATTCGGCCATCGCTGCTCCTGATCACAATGAAACGCTTTCGATCGCC
AAGAATATTGCCAAGACGTATGACGTTACGGGTTACGCATATACTGGTGGTGGTCGTCTCATCACCAGGGTCG
AAATTTCAGTTGATGGCGGTATCCATTGGGAACTTGCCAAACTTGAACGCAAGGAGCAGCCAACGGACTACGG
AATGTACTGGTGCTGGACTTGGTGGAACTACGAAGTAAAGGTGGCCGACTTGGTGGGAGCCAAGGAAATTATA
TGCCGCGCCTGGGATGAGTCCAACAACCCTCAGCCAGTTGTTCCAACATGGAATCTGATGGGTATGGGAAATA
ATCAAGCCTTTCGTGTCAAGGTACACATGGACAAGACAGCTAGCGGCGAGCATGTGTTTCGGTTTGAGCATCC
AACTCAGCCTGGTCAACAAACTGGTGGGTGGATGACAAAGGTCGCCACCAAGCCTGAGTCGGCTGGGTTCGGA
CGGTTGCTGGAAGTGCAGGGTGAGTCCAAAGAAGACGCGGCCCCGGCTCCACCTCCGAAGGAAAATACCAAAA
TTTTCACGATGGAAGAGATTGAAAAGCACAACACTGAAGAAGACTGTTGGATTGTGGTGAAGGATCGTGTCTA
CGACTGTACCGAGTATCTAGAGCTGCACCCTGGCGGCATTGACTCGATTGTTATCAACGGCGGCGCAGATTCC
ACGGAAGACTTTGTGGCAATCCACTCTACCAAGGCTACAAAGATGCTCGAGAAGTACTACATTGGCCAGCTCG
ACAAAAGTAGTGTGGCCGAGGAGAAAAAACAAGAAGACGAACCTCTCGTCGATGCCGATGGCAATGCTCTTGC
CTTGAACCCAAAGAAGAAGACGCCATTTCGTCTACAAAACAAAATCACACTTAGTCGAGACAGCTACCTATTG
GATTTTGCTTTGCCAAGCCCAAAGCATGTTTTGGGGCTACCCACGGGAAAGCACATGTTTATTCGGCCCTCA
TTAATGGAGAGATGGTACTCCGCCGCTACACTCCTATCTCATCCAATTACGACATTGGATGTGTAAAGTTTGT
TGTCAAGGCATACCGTCCGTGTGAACGCTTTCCAGACGGTGGCAAGATGAGCCAATACCTAGACCAGATCAAT
GTTGGCGACTATGTTGATATGCGCGGACCAGTTGGGGAATTTGAGTACTCGGCCAACGGCAGTTTTACAATCG
ACGCCGAACCTTGTTTTGCCACCAGGTTCAACATGCTTGCTGGGGGGACCGGCATAACGCCCGTAATGCAGAT
TGCTGCGGAAATTTTGCGAAACCCACAAGACCCTACACAAATGTCCCTTATTTTTGCATGCCGCGAGGAAGGC
GATCTCTTGATGCGAAGCACTTTGGACGAATGGGCTGCTAACTTTCCTCACAAGTTCAAGATTCACTACATCC
TATCTGACAGCTGGTCTTCCGACTGGAAGTATTCCACAGGATTCGTAGACAAAGCGCTATTTTCCGAGTACTT
GTACGAAGCAGGCGATGATGTTTACAGCCTCATGTGCGGCCCACCAATTATGTTAGAGAAAGGCTGCCGTCCA
AACTTGGAGAGCCTTGGTCACAAAAAGGACAAAATTTTTTCCTTTTAA

Figure 3 *Thalassiosira pseudonana* Nitrate reductase

A (SEQ ID NO: 3)
MAPINGMKRADTSESSVDLTTLIKPSTSIQNFKSISSSQPTKEQTCVDLYGPYPSSIPVPTISKDGSVPPTDV
TSKAKTMWDVQSYPDHRDVGTPDEWIPRDGKLVRLTGRHPFNVEPPLSVHQEHKFITPTCLHYVRNHGACPNI
KWEEHRVRVGGLVDTPLDLGMDEIVAMEPRELPVTLVCAGNRRKEQNMIRQTIGFNWGAGGVSTNVWKGVTLR
DLLLKAGVSEKNMAGKHVEFIGAEDLPNKVGPGPFKDEPWGKLVKYGTSVPLARAMNPAYDILIAYEANGEVL
QPDHGYPIRLIIPGYIGGRMIKWLTDINVLEHETKNHYHYHDNRILPPHITAEESLTGGWWYKPEYIFNELNI
NSAMTAPDHNETIDLASSIGSSYEVGGYAYTGGGRRISRVEVSTDGGVHWEIANINQIEKPTDYGMYWCWIWW
TFDLKVADLVGTKELWCRAWDESNNVQPNDPTWNLMGMGNNQVFRIKVHLDKDVNGKHVFRFEHPTKPGQQEG
GWMTTLAGKPDSAGFGRLLEQGQPAKEAAPAAAPAKTSGSKLIKMEEVRKHNKEEDVWIVVNNKVYDCTEYLD
LHPGGADSILINAGEDATEDFVAIHSTKATKMLDKFYVGDLDTTSVAVVSDAEEERLCPKTGRKVALDPKHKH
AFKLQTKTVLSRDSFELDFALQTPEHVLGLPTGKHVFLSADINGEMVMRRYTPTTSDHDIGQIKFVIKAYPPC
ERFPLGGKMSQYLDSLKVGDTIDMRGPVGEFDYHGNGKFLKEHDECYATHFNMIAGGTGITPVMQIASEILRN
PDDKTTMSLVFGCREEGDLLLRSTLDEWAVKHADRFKVHYVLSENAPPGWTHSIGFVSKELFEKELFPAGDNC
YNLMCGPPIMLERGCTPNLKALGHKEDNIFSF

B (SEQ ID NO: 4)
ATGGCACCCATCAACGGCATGAAACGAGCCGACACATCCGAGTCCTCCGTGGACCTCACCACCCTCATCAAAC
CGTCCACCTCCATCCAAAACTTTAAATCCATCTCCTCCTCCCAACCCACCAAAGAACAAACATGCGTCGACCT
CTACGGCCCCTACCCCTCCTCCATCCCCGTCCCCACCATCTCCAAAGACGGTAGCGTCCCACCCACCGACGTC
ACCTCCAAAGCCAAGACCATGTGGGACGTCCAATCCTACCCCGACCATCGTGACGTCGGTACACCCGACGAAT
GGATTCCACGCGATGGCAAATTAGTGAGGTTAACTGGACGTCATCCCTTCAACGTCGAACCTCCCTTGAGTGT
CCATCAAGAACACAAGTTCATCACTCCCACCTGTCTTCACTACGTTCGTAATCACGGAGCATGTCCCAATATC
AAGTGGGAGGAGCATCGTGTTCGTGTGGGTGGACTGGTGGATACGCCGCTTGATTTGGGGATGGATGAGATTG
TGGCGATGGAACCGAGGGAGCTTCCGGTGACGTTGGTGTGTGCTGGGAATAGGAGGAAGGAGCAGAATATGAT
TAGGCAGACGATTGGGTTTAATTGGGGTGCGGGAGGTGTTAGCACGAACGTTTGGAAGGGCGTTACTTTGAGG
GATTTGTTGTTGAAGGCTGGTGTTAGCGAGAAGAACATGGCGGGCAAACACGTTGAATTCATCGGAGCCGAAG
ACCTCCCCAACAAGGTAGGCCCCGGTCCATTCAAGGATGAACCATGGGGCAAACTCGTCAAATACGGTACTTC
CGTCCCTCTCGCACGTGCCATGAACCCCGCCTATGACATTCTCATCGCCTACGAAGCCAACGGAGAGGTACTT
CAACCGGATCACGGATATCCTATCCGTCTCATCATTCCTGGATACATTGGTGGAAGGATGATCAAGTGGCTTA
CGGATATCAATGTGTTGGAGCACGAGACGAAGAACCATTATCACTATCATGATAATCGTATCTTGCCTCCTCA
TATTACGGCCGAAGAGAGTTTGACAGGTGGATGGTGGTACAAGCCCGAGTACATCTTTAATGAGTTGAACATT
AACTCTGCCATGACTGCTCCTGATCACAATGAAACGATTGATCTGGCTTCCAGTATTGGAAGTTCCTACGAGG
TGGGAGGATATGCCTACACGGGAGGTGGACGTCGCATCTCCCGTGTCGAGGTATCTACCGATGGAGGAGTGCA
TTGGGAGATTGCCAATATTAACCAGATTGAGAAGCCAACCGATTATGGAATGTACTGGTGTTGGATCTGGTGG
ACGTTTGATCTCAAGGTTGCTGATTTAGTTGGAACGAAGGAACTCTGGTGTCGTGCTTGGGATGAATCCAACA
ACGTTCAGCCCAACGATCCTACCTGGAATCTCATGGGAATGGGAAACAACCAAGTCTTCCGTATCAAGGTCCA
TCTCGATAAGGATGTGAACGGAAAGCATGTCTTTAGGTTTGAGCATCCTACCAAGCCTGGACAGCAGGAGGGT
GGATGGATGACTACTCTCGCTGGAAAGCCGGATAGTGCTGGGTTCGGAAGGTTGTTGGAGCAAGGACAGCCTG
CGAAGGAGGCAGCACCTGCTGCGGCTCCTGCCAAGACTTCTGGTAGCAAGCTGATCAAGATGGAGGAGGTGAG
GAAGCATAACAAGGAGGAGGATGTTTGGATTGTGGTGAACAATAAGGTGTATGACTGTACCGAGTATTTGGAT
CTTCATCCTGGTGGAGCTGATTCCATCCTCATCAACGCTGGAGAGGATGCCACCGAAGATTTCGTCGCCATCC
ATTCTACCAAAGCAACCAAGATGTTGGACAAGTTCTACGTCGGCGACTTGGACACTACTTCAGTGGCGGTTGT
TTCTGATGCTGAGGAGGAACGTCTCTGCCCCAAGACAGGAAGGAAGGTGGCGTTGGATCCCAAGCACAAGCAT
GCCTTTAAACTTCAGACAAAGACCGTATTGTCTCGTGATTCTTTTGAGTTGGACTTTGCTCTTCAGACTCCCG
AGCACGTCCTTGGTTTGCCAACAGGAAAGCACGTCTTCCTGTCTGCGGATATCAACGGTGAGATGGTGATGCG
CCGATACACACCTACGACTTCCGATCACGACATTGGCCAAATCAAGTTCGTTATCAAAGCCTACCCACCTTGT
GAACGTTTCCCACTCGGAGGTAAGATGTCACAATACCTCGACTCTCTAAAGGTTGGAGATACCATCGATATGA
GAGGACCGGTCGGAGAGTTTGACTACCACGGCAACGGAAAGTTCCTCAAGGAGCACGACGAGTGTTACGCCAC
TCATTTCAACATGATTGCTGGAGGTACTGGTATCACTCCCGTTATGCAGATTGCTTCCGAGATCCTTCGCAAC
CCCGATGACAAGACTACCATGTCATTGGTCTTTGGATGTCGTGAGGAGGGTGATTTGCTTTTGAGATCAACTC
TTGACGAGTGGGCTGTGAAGCATGCCGATAGGTTCAAGGTTCACTATGTTCTCTCTGAAAATGCTCCTCCAGG
ATGGACTCACTCCATCGGATTCGTCAGCAAGGAGTTGTTTGAGAAGGAGTTGTTCCCCGCTGGCGACAACTGT
TACAATCTCATGTGTGGACCTCCAATCATGTTGGAGAGGGGGTGTACTCCCAACTTGAAGGCTCTTGGGCACA
AGGAGGATAACATCTTCTCATTCTAA

Figure 4 *Phaeodactylum tricornutum* Pyrenoid Decarboxylase

A (SEQ ID NO: 5)
MRMSTAALLCSVYTAGSTAAFAPALLTRRYSSSSSTLSATTNPLQSIFLTPETAKACIDAAGGTPLYAYSIDK
LEEAADACLAFPNAYGLTVRYAMKACPNASILKYFHSKNIHVDASSGFEVRRAMDAGVPAENISLSTQELPED
FAALVDMGVKLNACSVSQLERFGEHYAGKGAKVGVRVNPGVGSGGFSASTTGFSKTNVGGPSSSFGIWHELVT
DGTVPDIVERYGLEVERIHTHIGSGSDPEIWQQVATKSLSFCKVFPTVKTMNLGGGYKVGRNKGEVTTDLQKI
GKPVADAFKKFAEKEGRELQMEIEPGTYLVAMAGALVSKVQDKVHTTGENSHTFLKLDAGMTDVLRPSLYGAV
HPITILPGSGNSADVGDETESVVVVGHCCESGDLMTPAPGEPEQLAEQELRAAAVGDILVMDGSGAYCSGMST
KNYNSFPEAPEVLVDKAGKAHLIRKRQTLSQIYENEISVEGV

B (SEQ ID NO: 6)
ATGAGAATGTCTACTGCTGCTCTGCTCTGCTCAGTTTACACAGCCGGAAGCACTGCCGCGTTTGCTCCCGCTT
TGCTTACGCGGCGATACTCCTCGTCATCATCGACCTTGTCTGCTACGACGAATCCGTTACAGTCTATCTTTTT
GACGCCCGAAACTGCCAAGGCCTGCATTGATGCCGCCGGTGGGACACCTCTGTACGCGTACAGTATCGACAAG
CTGGAGGAAGCCGCCGATGCCTGTCTAGCTTTTCCCAACGCGTACGGACTGACGGTACGCTACGCCATGAAAG
CCTGTCCCAACGCGTCCATTCTCAAGTATTTTCACTCGAAAAATATTCACGTTGACGCATCTTCCGGTTTCGA
AGTACGCCGGGCGATGGATGCCGGTGTTCCGGCCGAAAATATCTCCCTGAGTACGCAGGAGTTGCCCGAAGAC
TTTGCGGCACTGGTTGATATGGGTGTCAAGCTCAATGCTTGTTCCGTCTCGCAGCTAGAGCGGTTCGGTGAGC
ACTATGCTGGAAAAGGTGCGAAGGTGGGCGTCCGAGTGAATCCGGGAGTGGGGTCGGGAGGCTTCTCCGCGAG
TACCACTGGATTCAGTAAAACTAATGTCGGCGGACCGAGCAGTTCGTTCGGGATTTGGCACGAACTCGTCACC
GATGGAACCGTCCCAGATATCGTGGAAAGGTACGGTTTGGAAGTGGAACGTATTCATACACATATTGGATCAG
GTAGTGATCCGGAGATTTGGCAGCAAGTTGCCACCAAATCCTTGTCCTTTTGCAAGGTGTTTCCCACCGTCAA
AACCATGAATCTTGGTGGCGGCTACAAGGTGGGACGCAACAAGGGCGAAGTTACGACAGATTTGCAGAAAATC
GGGAAGCCTGTGGCGGATGCCTTTAAAAAGTTCGCGGAAAAGGAAGGCCGGAATTGCAAATGGAAATTGAGC
CCGGAACTTATCTCGTGGCCATGGCTGGAGCACTCGTCTCCAAGGTCCAAGACAAGGTTCACACCACCGGAGA
GAATAGCCACACCTTCTTGAAGCTTGATGCCGGCATGACGGACGTCTTGCGCCCGAGCTTGTATGGTGCCGTG
CATCCTATTACGATTCTGCCCGGGTCGGGAAATTCTGCCGACGTTGGCGATGAAACCGAATCTGTAGTGGTGG
TTGGACATTGTTGTGAATCAGGGGACCTCATGACTCCGGCCCCGGGTGAGCCGGAACAACTAGCGGAACAAGA
ACTTCGTGCGGCAGCGGTAGGTGATATTCTAGTGATGGATGGCTCTGGGGCGTACTGCTCCGGCATGTCGACG
AAGAACTACAACAGCTTTCCCGAAGCACCAGAAGTGTTGGTGGACAAGGCAGGCAAGGCACACTTGATCCGTA
AACGACAAACCCTGAGTCAAATTTACGAGAACGAAATCTCCGTAGAAGGCGTGTTTTAA

Figure 5 *Thalassiosira pseudonana* Pyrenoid Decarboxylase

A (SEQ ID NO: 7)
MKVSSLAIVTALFATSTNAFSPIQPHSTTPIITTSQLHATPPSQSNFLTPELATTCIATAQGTPLYAYSLSQL
AAAATATLAFPNAFGLTVRYAMKACPNGSILKYFLSRGICIDASSGYEVRRAMSMGVPAEKISLSSQELPADF
DELIGLGVKINACSVSQLERIGKAFPNTSQKVGIRINPGVGSGGFSSSTTGFSKTNVGGPSSSFGIWHELVTD
GTVPDIVTKYGLEVERIHTHIGSGSDPAIWQSVATRSLSFCKLWDTITTLNLGGGYKVGRNPGEKTTDLNEIG
APVADAFRDFAKETGRELQMEIEPGTYLVANAGALVTTIQDKVSTKSASSDEGHIYLKMDAGMTDVLRPSLYG
AIHPITILPASGKSSDIGTATESVVVVGHCCESGDLMTPKPGEPEALEERVLRTAEIGDIAVMDGSGAYCAGM
STKNYNSFPEAPEVLVDLEGKVHLIRKRQSLQQIYENECDVPSGLF

B (SEQ ID NO: 8)
ATGAAGGTCTCCAGCCTCGCCATCGTAACGGCCCTATTCGCGACCTCCACCAATGCCTTCTCTCCGATCCAGC
CACACAGCACCACACCCATCATCACCACCTCTCAACTCCACGCCACGCCCCCTCCCAATCCAACTTCCTCAC
CCCCGAACTAGCCACCACCTGCATCGCCACCGCCCAAGGCACGCCCCTCTACGCCTACTCCCTCTCCCAACTA
GCCGCCGCCGCCACAGCCACCCTCGCCTTCCCCAACGCATTCGGTCTTACTGTACGATATGCCATGAAGGCGT
GTCCCAATGGAAGTATTTTGAAGTACTTTTTGAGTAGGGGGATTTGTATCGATGCGAGTTCCGGGTATGAAGT
GAGGAGAGCAATGAGTATGGGTGTTCCGGCCGAGAAGATTAGTTTGAGTTCGCAGGAGTTGCCGGCGGATTTT
GATGAGTTGATTGGTTTGGGGGTCAAGATTAATGCTTGCTCCGTATCCCAACTCGAACGCATCGGCAAAGCCT
TCCCCAACACCTCTCAAAAGGTAGGCATCCGCATCAACCCCGGCGTAGGATCCGGTGGATTCTCCTCCTCCAC
AACCGGCTTTTCCAAAACCAACGTCGGCGGTCCTTCCTCCTCCTTTGGTATCTGGCACGAACTCGTTACCGAT
GGAACCGTACCTGACATTGTAACCAAGTATGGATTGGAGGTGGAGAGGATTCACACCCACATCGGTTCGGGGT
CGGATCCTGCCATTTGGCAATCGGTTGCTACTCGCTCTTTGTCATTCTGTAAACTTTGGGATACAATCACAAC
ATTGAACCTCGGGGGAGGGTACAAGGTGGGAAGAAACCCGGGAGAGAAAACCACTGACTTGAATGAGATTGGG
GCCCCTGTTGCCGATGCGTTTAGGGACTTTGCAAAGGAGACGGGGAGGGAGTTGCAGATGGAGATCGAGCCGG
GCACGTATTTGGTTGCGAATGCTGGAGCTCTCGTGACGACGATTCAGGATAAGGTATCGACCAAATCGGCATC
CTCCGACGAAGGACACATTTACCTCAAAATGGATGCTGGTATGACGGATGTCCTTCGTCCTTCCCTCTACGGA
GCCATTCATCCAATCACAATCCTCCCCGCATCTGGAAAGTCATCTGACATTGGTACCGCTACCGAAAGTGTCG
TCGTTGTAGGACATTGTTGTGAATCTGGAGATCTCATGACACCCAAACCTGGTGAGCCCGAGGCATTGGAAGA
ACGTGTTCTCCGTACTGCCGAGATTGGTGATATTGCCGTGATGGATGGAAGTGGAGCTTACTGTGCTGGAATG
TCGACTAAGAATTACAATAGTTTCCCCGAGGCGCCGGAGGTGTTGGTTGATTTGGAAGGAAAGGTTCATTTGA
TAAGGAAGAGGCAGAGTTTGCAGCAGATTTACGAGAATGAGTGTGATGTTCCCAGTGGTCTCTTTTGA

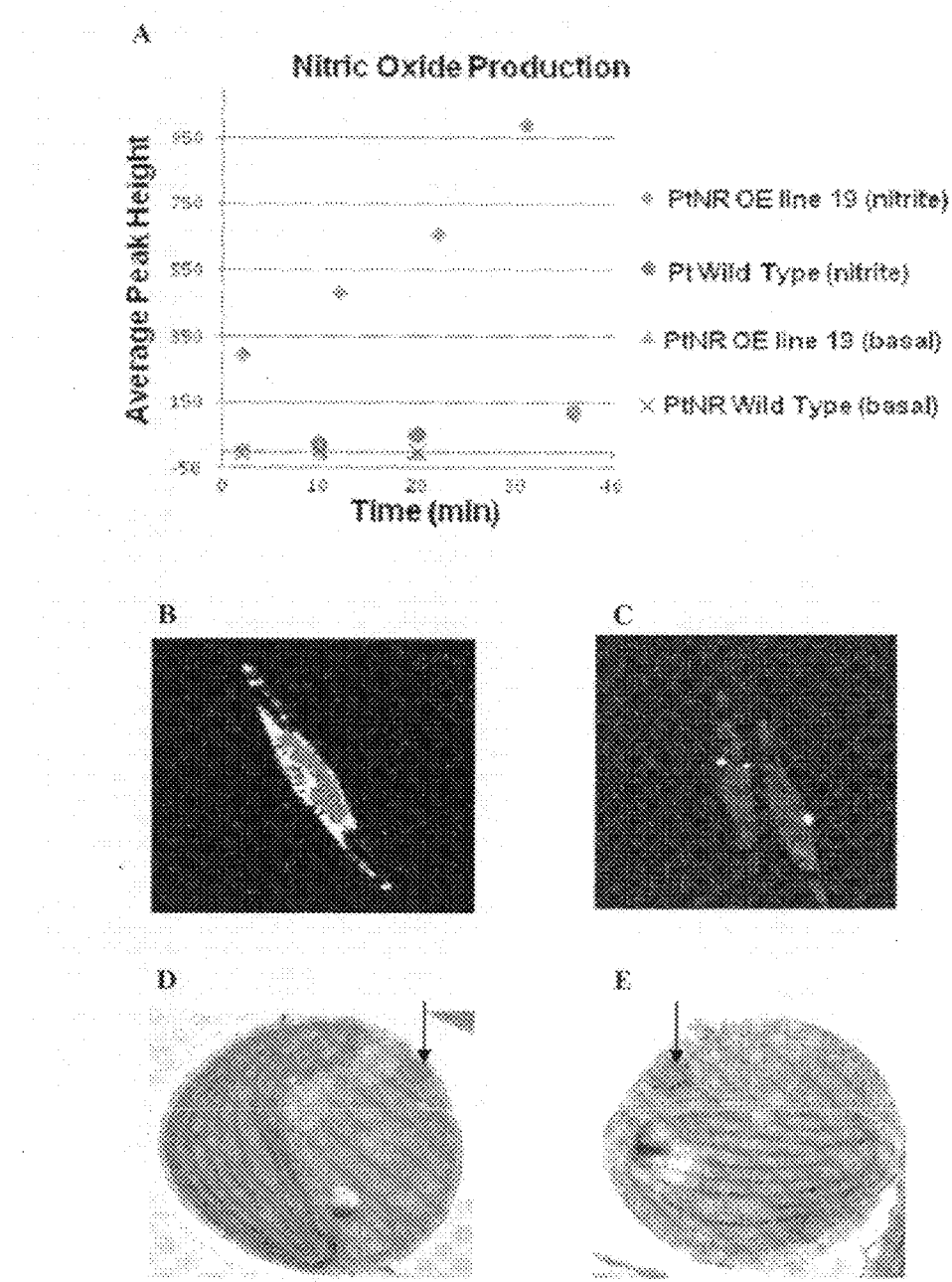

SEQUENCE LISTING

```
<160> NUMBER OF SEQ ID NOS: 8

<210> SEQ ID NO 1
<211> LENGTH: 891
<212> TYPE: PRT
<213> ORGANISM: Phaeodactylum tricornutum

<400> SEQUENCE: 1

Met Val Pro Lys Pro Glu Asp Pro Thr Val Lys Ala Glu Asn Asn Ala
1               5                   10                  15

Ala Met Asp Gln Leu Ser Leu Leu Asp Lys Asp Asp Ile Ser Ser Ala
            20                  25                  30

Ser Arg Ser Cys Arg Glu Leu Tyr Gly Pro Tyr Pro Lys Ala Ile Pro
        35                  40                  45
```

-continued

```
Val Pro Phe Leu Asn Ser Arg Asn Glu Ala Arg Glu Gly Asp Thr Pro
 50                  55                  60

Ala Ala Ser Val Ile Ala Gln Ala Lys Thr Ile Phe Asp Val Pro Ala
 65                  70                  75                  80

Asp Tyr Arg Asp Val Gly Thr Pro Asp Glu Trp Val Pro Arg Asp Gly
                     85                  90                  95

Arg Leu Val Arg Leu Thr Gly Lys His Pro Phe Asn Val Glu Pro Pro
                100                 105                 110

Leu Ala Ile Leu Lys Gln His Arg Phe Ile Thr Pro Ser Ser Leu His
                115                 120                 125

Tyr Val Arg Asn His Gly Ala Cys Pro Lys Leu Ser Trp Lys Glu His
            130                 135                 140

Thr Val Cys Val Gly Gly Lys Leu Val Pro Asn Ala Leu Glu Leu Ser
145                 150                 155                 160

Met Asp Glu Ile Val Ala Met Glu Pro Arg Glu Leu Pro Val Thr Leu
                    165                 170                 175

Val Cys Ala Gly Asn Arg Arg Lys Glu Gln Asn Met Ile Arg Gln Thr
                180                 185                 190

Ile Gly Phe Asn Trp Gly Pro Ser Gly Val Ser Thr Ser Val Trp Lys
            195                 200                 205

Gly Val Leu Leu Arg Asp Leu Leu Arg Ala Gly Val Ser Glu Lys
            210                 215                 220

Asn Met Ala Gly Lys His Val Glu Phe Ile Gly Val Glu Asp Leu Pro
225                 230                 235                 240

Asn Lys Val Gly Pro Gly Pro Phe Gln Glu Glu Pro Trp Gly Lys Leu
                    245                 250                 255

Val Lys Tyr Gly Thr Ser Val Pro Leu Ala Arg Ala Met Asn Pro Ala
                260                 265                 270

Tyr Asp Ile Leu Ile Ala Tyr Glu Gln Asn Gly Glu Val Leu Gln Pro
            275                 280                 285

Asp His Gly Tyr Pro Val Arg Leu Ile Ile Pro Gly Tyr Ile Gly Gly
            290                 295                 300

Arg Met Ile Lys Trp Leu Lys Tyr Ile Asn Val Ile Pro His Glu Thr
305                 310                 315                 320

Lys Asn His Tyr His Tyr His Asp Asn Arg Ile Leu Pro Gly Gly Trp
                    325                 330                 335

Trp Tyr Lys Pro Glu Tyr Ile Phe Asn Glu Leu Asn Ile Asn Ser Ala
                340                 345                 350

Ile Ala Ala Pro Asp His Asn Glu Thr Leu Ser Ile Ala Lys Asn Ile
            355                 360                 365

Ala Lys Thr Tyr Asp Val Thr Gly Tyr Ala Tyr Thr Gly Gly Gly Arg
            370                 375                 380

Leu Ile Thr Arg Val Glu Ile Ser Val Asp Gly Gly Ile His Trp Glu
385                 390                 395                 400

Leu Ala Lys Leu Glu Arg Lys Glu Gln Pro Thr Asp Tyr Gly Met Tyr
                    405                 410                 415

Trp Cys Trp Thr Trp Asn Tyr Glu Val Lys Val Ala Asp Leu Val
                420                 425                 430

Gly Ala Lys Glu Ile Ile Cys Arg Ala Trp Asp Glu Ser Asn Asn Pro
            435                 440                 445

Gln Pro Val Val Pro Thr Trp Asn Leu Met Gly Met Gly Asn Asn Gln
450                 455                 460

Ala Phe Arg Val Lys Val His Met Asp Lys Thr Ala Ser Gly Glu His
```

```
            465                 470                 475                 480
        Val Phe Arg Phe Glu His Pro Thr Gln Pro Gly Gln Gln Thr Gly Gly
                        485                 490                 495

Trp Met Thr Lys Val Ala Thr Lys Pro Glu Ser Ala Gly Phe Gly Arg
                        500                 505                 510

Leu Leu Glu Val Gln Gly Glu Ser Lys Glu Asp Ala Ala Pro Ala Pro
                        515                 520                 525

Pro Pro Lys Glu Asn Thr Lys Ile Phe Thr Met Glu Glu Ile Glu Lys
                        530                 535                 540

His Asn Thr Glu Glu Asp Cys Trp Ile Val Lys Asp Arg Val Tyr
        545                 550                 555                 560

Asp Cys Thr Glu Tyr Leu Glu Leu His Pro Gly Ile Asp Ser Ile
                        565                 570                 575

Val Ile Asn Gly Gly Ala Asp Ser Thr Glu Asp Phe Val Ala Ile His
                        580                 585                 590

Ser Thr Lys Ala Thr Lys Met Leu Glu Lys Tyr Tyr Ile Gly Gln Leu
                        595                 600                 605

Asp Lys Ser Ser Val Ala Glu Glu Lys Lys Gln Glu Asp Glu Pro Leu
                        610                 615                 620

Val Asp Ala Asp Gly Asn Ala Leu Ala Leu Asn Pro Lys Lys Lys Thr
        625                 630                 635                 640

Pro Phe Arg Leu Gln Asn Lys Ile Thr Leu Ser Arg Asp Ser Tyr Leu
                        645                 650                 655

Leu Asp Phe Ala Leu Pro Ser Pro Lys His Val Leu Gly Leu Pro Thr
                        660                 665                 670

Gly Lys His Met Phe Ile Ser Ala Leu Ile Asn Gly Glu Met Val Leu
                        675                 680                 685

Arg Arg Tyr Thr Pro Ile Ser Ser Asn Tyr Asp Ile Gly Cys Val Lys
                        690                 695                 700

Phe Val Val Lys Ala Tyr Arg Pro Cys Glu Arg Phe Pro Asp Gly Gly
        705                 710                 715                 720

Lys Met Ser Gln Tyr Leu Asp Gln Ile Asn Val Gly Asp Tyr Val Asp
                        725                 730                 735

Met Arg Gly Pro Val Gly Glu Phe Glu Tyr Ser Ala Asn Gly Ser Phe
                        740                 745                 750

Thr Ile Asp Ala Glu Pro Cys Phe Ala Thr Arg Phe Asn Met Leu Ala
                        755                 760                 765

Gly Gly Thr Gly Ile Thr Pro Val Met Gln Ile Ala Ala Glu Ile Leu
                        770                 775                 780

Arg Asn Pro Gln Asp Pro Thr Gln Met Ser Leu Ile Phe Ala Cys Arg
        785                 790                 795                 800

Glu Glu Gly Asp Leu Leu Met Arg Ser Thr Leu Asp Glu Trp Ala Ala
                        805                 810                 815

Asn Phe Pro His Lys Phe Lys Ile His Tyr Ile Leu Ser Asp Ser Trp
                        820                 825                 830

Ser Ser Asp Trp Lys Tyr Ser Thr Gly Phe Val Asp Lys Ala Leu Phe
                        835                 840                 845

Ser Glu Tyr Leu Tyr Glu Ala Gly Asp Asp Val Tyr Ser Leu Met Cys
                        850                 855                 860

Gly Pro Pro Ile Met Leu Glu Lys Gly Cys Arg Pro Asn Leu Glu Ser
        865                 870                 875                 880

Leu Gly His Lys Lys Asp Lys Ile Phe Ser Phe
                        885                 890
```

<210> SEQ ID NO 2
<211> LENGTH: 2676
<212> TYPE: DNA
<213> ORGANISM: Phaeodactylum tricornutum

<400> SEQUENCE: 2

| | | | | | |
|---|---|---|---|---|---|
| atggtaccga | aacctgaaga | tcccacagtc | aaggcagaga | ataatgcggc gatggatcaa | 60 |
| cttagtctcc | tcgacaaaga | tgatatatcg | tcggcttctc | gctcgtgccg agaactctac | 120 |
| ggaccttacc | ccaaagctat | tcctgtgccg | ttcttgaatt | ctcgtaacga agctcgcgaa | 180 |
| ggtgacactc | ccgccgccag | cgtcatcgcg | caagccaaaa | ccatctttga cgtaccggcg | 240 |
| gactatcgtg | acgtgggaac | accggatgaa | tgggttcccc | gcgatggacg cctcgtgcgt | 300 |
| ctgacgggta | agcatccctt | caacgtcgaa | ccaccgctgg | cgattctgaa gcagcatcga | 360 |
| tttattacgc | cgtcctcgtt | gcattacgta | cgcaaccacg | gagcgtgccc gaagctgtct | 420 |
| tggaaagaac | acactgtttg | tgtgggagga | aaactggtac | cgaatgcctt ggagctctcg | 480 |
| atggacgaaa | tcgtagcgat | ggaaccgcga | gagctgcccg | tcacgttggt ctgtgccgga | 540 |
| aatcgtcgga | aggaacaaaa | catgatccgt | caaacaatcg | gcttcaactg ggcccgagc | 600 |
| ggcgtctcaa | ccagcgtttg | aagggagtg | ctcctacgcg | atttgttgct ccgcgcaggg | 660 |
| gtttcggaaa | agaacatggc | agggaagcac | gtcgaattta | ttggtgtcga agacttgccg | 720 |
| aacaaggtgg | gacccgggcc | gttccaggag | gaaccatggg | gcaaacttgt caagtacgga | 780 |
| accagtgtcc | cgctcgctcg | ggctatgaat | ccagcgtacg | acatcctcat tgcctatgag | 840 |
| cagaacggcg | aagtcttgca | gcccgatcac | ggctaccccg | tccgtctcat cattcctggt | 900 |
| tatattggag | acggatgat | taaatggctt | aaatacatca | acgtgattcc gcacgaaacc | 960 |
| aagaatcact | atcattacca | cgacaatcgc | attttaccgg | gaggttggtg gtacaaaccg | 1020 |
| gagtacattt | tcaatgaact | caacatcaat | tcggccatcg | ctgctcctga tcacaatgaa | 1080 |
| acgctttcga | tcgccaagaa | tattgccaag | acgtatgacg | ttacgggtta cgcatatact | 1140 |
| ggtggtggtc | gtctcatcac | cagggtcgaa | atttcagttg | atggcggtat ccattgggaa | 1200 |
| cttgccaaac | ttgaacgcaa | ggagcagcca | acggactacg | aatgtactg gtgctggact | 1260 |
| tggtggaact | acgaagtaaa | ggtggccgac | ttggtgggag | ccaaggaaat tatatgccgc | 1320 |
| gcctgggatg | agtccaacaa | ccctcagcca | gttgttccaa | catggaatct gatgggtatg | 1380 |
| ggaaataatc | aagcctttcg | tgtcaaggta | cacatggaca | agacagctag cggcgagcat | 1440 |
| gtgtttcggt | ttgagcatcc | aactcagcct | ggtcaacaaa | ctggtgggtg gatgacaaag | 1500 |
| gtcgccacca | agcctgagtc | ggctgggttc | ggacggttgc | tggaagtgca gggtgagtcc | 1560 |
| aaagaagacg | cggccccggc | tccacctccg | aaggaaaata | ccaaaatttt cacgatggaa | 1620 |
| gagattgaaa | agcacaacac | tgaagaagac | tgttggattg | tggtgaagga tcgtgtctac | 1680 |
| gactgtaccg | agtatctaga | gctgcaccct | ggcggcattg | actcgattgt tatcaacggc | 1740 |
| ggcgcagatt | ccacggaaga | ctttgtggca | atccactcta | ccaaggctac aaagatgctc | 1800 |
| gagaagtact | acattggcca | gctcgacaaa | agtagtgtgg | ccgaggagaa aaaacaagaa | 1860 |
| gacgaacctc | tcgtcgatgc | cgatggcaat | gctcttgcct | tgaacccaaa gaagaagacg | 1920 |
| ccatttcgtc | tacaaaacaa | aatcacactt | agtcgagaca | gctacctatt ggattttgct | 1980 |
| ttgccaagcc | caaagcatgt | tttggggcta | cccacgggaa | agcacatgtt tatttcggcc | 2040 |
| ctcattaatg | gagagatggt | actccgccgc | tacactccta | tctcatccaa ttacgacatt | 2100 |

-continued

| | |
|---|---|
| ggatgtgtaa agtttgttgt caaggcatac cgtccgtgtg aacgctttcc agacggtggc | 2160 |
| aagatgagcc aatacctaga ccagatcaat gttggcgact atgttgatat gcgcggacca | 2220 |
| gttggggaat tgagtactc ggccaacggc agttttacaa tcgacgccga accttgtttt | 2280 |
| gccaccaggt tcaacatgct tgctgggggg accggcataa cgcccgtaat gcagattgct | 2340 |
| gcggaaattt tgcgaaaccc acaagaccct acacaaatgt cccttatttt tgcatgccgc | 2400 |
| gaggaaggcg atctcttgat gcgaagcact tggacgaat gggctgctaa ctttcctcac | 2460 |
| aagttcaaga ttcactacat cctatctgac agctggtctt ccgactggaa gtattccaca | 2520 |
| ggattcgtag acaaagcgct attttccgag tacttgtacg aagcaggcga tgatgtttac | 2580 |
| agcctcatgt gcggcccacc aattatgtta gagaaaggct gccgtccaaa cttggagagc | 2640 |
| cttggtcaca aaaggacaa aatttttcc ttttaa | 2676 |

<210> SEQ ID NO 3
<211> LENGTH: 908
<212> TYPE: PRT
<213> ORGANISM: Thalassiosira pseudonana

<400> SEQUENCE: 3

```
Met Ala Pro Ile Asn Gly Met Lys Arg Ala Asp Thr Ser Glu Ser Ser
 1               5                  10                  15

Val Asp Leu Thr Thr Leu Ile Lys Pro Ser Thr Ser Ile Gln Asn Phe
            20                  25                  30

Lys Ser Ile Ser Ser Ser Gln Pro Thr Lys Glu Gln Thr Cys Val Asp
        35                  40                  45

Leu Tyr Gly Pro Tyr Pro Ser Ser Ile Pro Val Pro Thr Ile Ser Lys
    50                  55                  60

Asp Gly Ser Val Pro Pro Thr Asp Val Thr Ser Lys Ala Lys Thr Met
65                  70                  75                  80

Trp Asp Val Gln Ser Tyr Pro Asp His Arg Asp Val Gly Thr Pro Asp
                85                  90                  95

Glu Trp Ile Pro Arg Asp Gly Lys Leu Val Arg Leu Thr Gly Arg His
            100                 105                 110

Pro Phe Asn Val Glu Pro Pro Leu Ser Val His Gln Glu His Lys Phe
        115                 120                 125

Ile Thr Pro Thr Cys Leu His Tyr Val Arg Asn His Gly Ala Cys Pro
    130                 135                 140

Asn Ile Lys Trp Glu Glu His Arg Val Arg Val Gly Gly Leu Val Asp
145                 150                 155                 160

Thr Pro Leu Asp Leu Gly Met Asp Glu Ile Val Ala Met Glu Pro Arg
                165                 170                 175

Glu Leu Pro Val Thr Leu Val Cys Ala Gly Asn Arg Arg Lys Glu Gln
            180                 185                 190

Asn Met Ile Arg Gln Thr Ile Gly Phe Asn Trp Gly Ala Gly Gly Val
        195                 200                 205

Ser Thr Asn Val Trp Lys Gly Val Thr Leu Arg Asp Leu Leu Leu Lys
    210                 215                 220

Ala Gly Val Ser Glu Lys Asn Met Ala Gly Lys His Val Glu Phe Ile
225                 230                 235                 240

Gly Ala Glu Asp Leu Pro Asn Lys Val Gly Pro Gly Phe Lys Asp
                245                 250                 255

Glu Pro Trp Gly Lys Leu Val Lys Tyr Gly Thr Ser Val Pro Leu Ala
            260                 265                 270
```

-continued

```
Arg Ala Met Asn Pro Ala Tyr Asp Ile Leu Ile Ala Tyr Glu Ala Asn
            275                 280                 285
Gly Glu Val Leu Gln Pro Asp His Gly Tyr Pro Ile Arg Leu Ile Ile
        290                 295                 300
Pro Gly Tyr Ile Gly Gly Arg Met Ile Lys Trp Leu Thr Asp Ile Asn
305                 310                 315                 320
Val Leu Glu His Glu Thr Lys Asn His Tyr His Tyr His Asp Asn Arg
                325                 330                 335
Ile Leu Pro Pro His Ile Thr Ala Glu Ser Leu Thr Gly Gly Trp
            340                 345                 350
Trp Tyr Lys Pro Glu Tyr Ile Phe Asn Glu Leu Asn Ile Asn Ser Ala
        355                 360                 365
Met Thr Ala Pro Asp His Asn Glu Thr Ile Asp Leu Ala Ser Ser Ile
    370                 375                 380
Gly Ser Ser Tyr Glu Val Gly Gly Tyr Ala Tyr Thr Gly Gly Gly Arg
385                 390                 395                 400
Arg Ile Ser Arg Val Glu Val Ser Thr Asp Gly Gly Val His Trp Glu
                405                 410                 415
Ile Ala Asn Ile Asn Gln Ile Glu Lys Pro Thr Asp Tyr Gly Met Tyr
            420                 425                 430
Trp Cys Trp Ile Trp Trp Thr Phe Asp Leu Lys Val Ala Asp Leu Val
        435                 440                 445
Gly Thr Lys Glu Leu Trp Cys Arg Ala Trp Asp Glu Ser Asn Asn Val
    450                 455                 460
Gln Pro Asn Asp Pro Thr Trp Asn Leu Met Gly Met Gly Asn Asn Gln
465                 470                 475                 480
Val Phe Arg Ile Lys Val His Leu Asp Lys Asp Val Asn Gly Lys His
                485                 490                 495
Val Phe Arg Phe Glu His Pro Thr Lys Pro Gly Gln Gln Glu Gly Gly
            500                 505                 510
Trp Met Thr Thr Leu Ala Gly Lys Pro Asp Ser Ala Gly Phe Gly Arg
        515                 520                 525
Leu Leu Glu Gln Gly Gln Pro Ala Lys Glu Ala Ala Pro Ala Ala Ala
    530                 535                 540
Pro Ala Lys Thr Ser Gly Ser Lys Leu Ile Lys Met Glu Glu Val Arg
545                 550                 555                 560
Lys His Asn Lys Glu Glu Asp Val Trp Ile Val Asn Asn Lys Val
                565                 570                 575
Tyr Asp Cys Thr Glu Tyr Leu Asp Leu His Pro Gly Gly Ala Asp Ser
            580                 585                 590
Ile Leu Ile Asn Ala Gly Glu Asp Ala Thr Glu Asp Phe Val Ala Ile
        595                 600                 605
His Ser Thr Lys Ala Thr Lys Met Leu Asp Lys Phe Tyr Val Gly Asp
    610                 615                 620
Leu Asp Thr Thr Ser Val Ala Val Ser Asp Ala Glu Glu Arg
625                 630                 635                 640
Leu Cys Pro Lys Thr Gly Arg Lys Val Ala Leu Asp Pro Lys His Lys
                645                 650                 655
His Ala Phe Lys Leu Gln Thr Lys Thr Val Leu Ser Arg Asp Ser Phe
            660                 665                 670
Glu Leu Asp Phe Ala Leu Gln Thr Pro Glu His Val Leu Gly Leu Pro
        675                 680                 685
Thr Gly Lys His Val Phe Leu Ser Ala Asp Ile Asn Gly Glu Met Val
```

Met Arg Arg Tyr Thr Pro Thr Thr Ser Asp His Asp Ile Gly Gln Ile
705             710                 715                 720

Lys Phe Val Ile Lys Ala Tyr Pro Pro Cys Glu Arg Phe Pro Leu Gly
                725                 730                 735

Gly Lys Met Ser Gln Tyr Leu Asp Ser Leu Lys Val Gly Asp Thr Ile
            740                 745                 750

Asp Met Arg Gly Pro Val Gly Glu Phe Asp Tyr His Gly Asn Gly Lys
        755                 760                 765

Phe Leu Lys Glu His Asp Glu Cys Tyr Ala Thr His Phe Asn Met Ile
    770                 775                 780

Ala Gly Gly Thr Gly Ile Thr Pro Val Met Gln Ile Ala Ser Glu Ile
785             790                 795                 800

Leu Arg Asn Pro Asp Asp Lys Thr Thr Met Ser Leu Val Phe Gly Cys
                805                 810                 815

Arg Glu Glu Gly Asp Leu Leu Leu Arg Ser Thr Leu Asp Glu Trp Ala
            820                 825                 830

Val Lys His Ala Asp Arg Phe Lys Val His Tyr Val Leu Ser Glu Asn
        835                 840                 845

Ala Pro Pro Gly Trp Thr His Ser Ile Gly Phe Val Ser Lys Glu Leu
    850                 855                 860

Phe Glu Lys Glu Leu Phe Pro Ala Gly Asp Asn Cys Tyr Asn Leu Met
865             870                 875                 880

Cys Gly Pro Pro Ile Met Leu Glu Arg Gly Cys Thr Pro Asn Leu Lys
                885                 890                 895

Ala Leu Gly His Lys Glu Asp Asn Ile Phe Ser Phe
            900                 905

<210> SEQ ID NO 4
<211> LENGTH: 2727
<212> TYPE: DNA
<213> ORGANISM: Thalassiosira pseudonana

<400> SEQUENCE: 4
atggcaccca tcaacggcat gaaacgagcc gacacatccg agtcctccgt ggacctcacc       60
accctcatca aaccgtccac ctccatccaa aactttaaat ccatctcctc ctcccaaccc      120
accaaagaac aaacatgcgt cgacctctac ggccccaccc cctcctccat ccccgtcccc      180
accatctcca agacggtag cgtcccaccc accgacgtca cctccaaagc caagaccatg       240
tgggacgtcc aatcctaccc cgaccatcgt gacgtcggta cacccgacga atggattcca      300
cgcgatggca aattagtgag gttaactgga cgtcatccct tcaacgtcga acctcccttg      360
agtgtccatc aagaacacaa gttcatcact cccacctgtc ttcactacgt tcgtaatcac      420
ggagcatgtc ccaatatcaa gtgggaggag catcgtgttc gtgtgggtgg actggtggat      480
acgccgcttg atttggggat ggatgagatt gtggcgatgg aaccgaggga gcttccggtg      540
acgttggtgt gtgctgggaa taggaggaag gagcagaata tgattaggca gacgattggg      600
tttaattggg gtgcgggagg tgttagcacg aacgtttgga agggcgttac tttgaggggat     660 ttgttgttga aggctggtgt tagcgagaag aacatggcgg gcaaacacgt tgaattcatc      720
ggagccgaag acctccccaa caaggtaggc cccggtccat tcaaggatga accatggggc      780
aaactcgtca aataccggtac ttccgtccct ctcgcacgtg ccatgaaccc cgcctatgac      840
attctcatcg cctacgaagc caacggagag gtacttcaac cggatcacgg atatcctatc      900

```
cgtctcatca ttcctggata cattggtgga aggatgatca agtggcttac ggatatcaat    960
gtgttggagc acgagacgaa gaaccattat cactatcatg ataatcgtat cttgcctcct   1020
catattacgg ccgaagagag tttgacaggt ggatggtggt acaagcccga gtacatcttt   1080
aatgagttga acattaactc tgccatgact gctcctgatc acaatgaaac gattgatctg   1140
gcttccagta ttggaagttc ctacgaggtg ggaggatatg cctacacggg aggtggacgt   1200
cgcatctccc gtgtcgaggt atctaccgat ggaggagtgc attgggagat tgccaatatt   1260
aaccagattg agaagccaac cgattatgga atgtactggt gttggatctg gtggacgttt   1320
gatctcaagg ttgctgattt agttggaacg aaggaactct ggtgtcgtgc ttgggatgaa   1380
tccaacaacg ttcagcccaa cgatcctacc tggaatctca tgggaatggg aaacaaccaa   1440
gtcttccgta tcaaggtcca tctcgataag gatgtgaacg gaaagcatgt ctttaggttt   1500
gagcatccta ccaagcctgg acagcaggag ggtggatgga tgactactct cgctggaaag   1560
ccggatagtg ctgggttcgg aaggttgttg gagcaaggac agcctgcgaa ggaggcagca   1620
cctgctgcgg ctcctgccaa gacttctggt agcaagctga tcaagatgga ggaggtgagg   1680
aagcataaca aggaggagga tgtttggatt gtggtgaaca ataaggtgta tgactgtacc   1740
gagtatttgg atcttcatcc tggtggagct gattccatcc tcatcaacgc tggagaggat   1800
gccaccgaag atttcgtcgc catccattct accaaagcaa ccaagatgtt ggacaagttc   1860
tacgtcggcg acttggacac tacttcagtg cggttgtttc tgatgctgga ggaacgt     1920
ctctgcccca agacaggaag gaaggtggcg ttggatccca agcacaagca tgcctttaaa   1980
cttcagacaa agaccgtatt gtctcgtgat tcttttgagt tggactttgc tcttcagact   2040
cccgagcacg tccttggttt gccaacagga agcacgtct tcctgtctgc ggatatcaac    2100
ggtgagatgg tgatgcgccg atacacacct acgacttccg atcacgacat tggccaaatc   2160
aagttcgtta tcaaagccta cccaccttgt gaacgtttcc cactcggagg taagatgtca   2220
caatacctcg actctctaaa ggttggagat accatcgata tgagaggacc ggtcggagag   2280
tttgactacc acggcaacgg aaagttcctc aaggagcacg acgagtgtta cgccactcat   2340
ttcaacatga ttgctggagg tactggtatc actcccgtta tgcagattgc ttccgagatc   2400
cttcgcaacc ccgatgacaa gactaccatg tcattggtct ttggatgtcg tgaggagggt   2460
gatttgcttt tgagatcaac tcttgacgag tgggctgtga agcatgccga taggttcaag   2520
gttcactatg ttctctctga aaatgctcct ccaggatgga ctcactccat cggattcgtc   2580
agcaaggagt gtttgagaa ggagttgttc cccgctggcg acaactgtta caatctcatg    2640
tgtggacctc caatcatgtt ggagaggggg tgtactccca acttgaaggc tcttgggcac   2700
aaggaggata acatcttctc attctaa                                       2727
```

<210> SEQ ID NO 5
<211> LENGTH: 480
<212> TYPE: PRT
<213> ORGANISM: Phaeodactylum tricornutum

<400> SEQUENCE: 5

Met Arg Met Ser Thr Ala Ala Leu Leu Cys Ser Val Tyr Thr Ala Gly
1               5                   10                  15

Ser Thr Ala Ala Phe Ala Pro Ala Leu Leu Thr Arg Arg Tyr Ser Ser
            20                  25                  30

Ser Ser Ser Thr Leu Ser Ala Thr Thr Asn Pro Leu Gln Ser Ile Phe
        35                  40                  45

-continued

```
Leu Thr Pro Glu Thr Ala Lys Ala Cys Ile Asp Ala Ala Gly Gly Thr
 50                  55                  60

Pro Leu Tyr Ala Tyr Ser Ile Asp Lys Leu Glu Glu Ala Ala Asp Ala
 65                  70                  75                  80

Cys Leu Ala Phe Pro Asn Ala Tyr Gly Leu Thr Val Arg Tyr Ala Met
                 85                  90                  95

Lys Ala Cys Pro Asn Ala Ser Ile Leu Lys Tyr Phe His Ser Lys Asn
            100                 105                 110

Ile His Val Asp Ala Ser Ser Gly Phe Glu Val Arg Ala Met Asp
        115                 120                 125

Ala Gly Val Pro Ala Glu Asn Ile Ser Leu Ser Thr Gln Glu Leu Pro
130                 135                 140

Glu Asp Phe Ala Ala Leu Val Asp Met Gly Val Lys Leu Asn Ala Cys
145                 150                 155                 160

Ser Val Ser Gln Leu Glu Arg Phe Gly Glu His Tyr Ala Gly Lys Gly
                165                 170                 175

Ala Lys Val Gly Val Arg Val Asn Pro Gly Val Gly Ser Gly Gly Phe
            180                 185                 190

Ser Ala Ser Thr Thr Gly Phe Ser Lys Thr Asn Val Gly Gly Pro Ser
        195                 200                 205

Ser Ser Phe Gly Ile Trp His Glu Leu Val Thr Asp Gly Thr Val Pro
210                 215                 220

Asp Ile Val Glu Arg Tyr Gly Leu Glu Val Glu Arg Ile His Thr His
225                 230                 235                 240

Ile Gly Ser Gly Ser Asp Pro Glu Ile Trp Gln Gln Val Ala Thr Lys
                245                 250                 255

Ser Leu Ser Phe Cys Lys Val Phe Pro Thr Val Lys Thr Met Asn Leu
            260                 265                 270

Gly Gly Gly Tyr Lys Val Gly Arg Asn Lys Gly Glu Val Thr Thr Asp
        275                 280                 285

Leu Gln Lys Ile Gly Lys Pro Val Ala Asp Ala Phe Lys Lys Phe Ala
290                 295                 300

Glu Lys Glu Gly Arg Glu Leu Gln Met Glu Ile Glu Pro Gly Thr Tyr
305                 310                 315                 320

Leu Val Ala Met Ala Gly Ala Leu Val Ser Lys Val Gln Asp Lys Val
                325                 330                 335

His Thr Thr Gly Glu Asn Ser His Thr Phe Leu Lys Leu Asp Ala Gly
            340                 345                 350

Met Thr Asp Val Leu Arg Pro Ser Leu Tyr Gly Ala Val His Pro Ile
        355                 360                 365

Thr Ile Leu Pro Gly Ser Gly Asn Ser Ala Asp Val Gly Asp Glu Thr
370                 375                 380

Glu Ser Val Val Val Gly His Cys Cys Glu Ser Gly Asp Leu Met
385                 390                 395                 400

Thr Pro Ala Pro Gly Glu Pro Glu Gln Leu Ala Glu Gln Glu Leu Arg
                405                 410                 415

Ala Ala Ala Val Gly Asp Ile Leu Val Met Asp Gly Ser Gly Ala Tyr
            420                 425                 430

Cys Ser Gly Met Ser Thr Lys Asn Tyr Asn Ser Phe Pro Glu Ala Pro
        435                 440                 445

Glu Val Leu Val Asp Lys Ala Gly Lys Ala His Leu Ile Arg Lys Arg
450                 455                 460

Gln Thr Leu Ser Gln Ile Tyr Glu Asn Glu Ile Ser Val Glu Gly Val
```

<210> SEQ ID NO 6
<211> LENGTH: 1446
<212> TYPE: DNA
<213> ORGANISM: Phaeodactylum tricornutum

<400> SEQUENCE: 6

```
atgagaatgt ctactgctgc tctgctctgc tcagtttaca cagccggaag cactgccgcg      60
tttgctcccg ctttgcttac gcggcgatac tcctcgtcat catcgacctt gtctgctacg     120
acgaatccgt tacagtctat cttttttgacg cccgaaactg ccaaggcctg cattgatgcc     180
gccggtggga cacctctgta cgcgtacagt atcgacaagc tggaggaagc cgccgatgcc     240
tgtctagctt tccccaacgc gtacggactg acggtacgct acgccatgaa agcctgtccc     300
aacgcgtcca ttctcaagta ttttcactcg aaaaatattc acgttgacgc atcttccggt     360
ttcgaagtac gccgggcgat ggatgccggt gttccggccg aaaatatctc cctgagtacg     420
caggagttgc ccgaagactt tgcggcactg gttgatatgg tgtcaagct caatgcttgt     480
tccgtctcgc agctagagcg gttcggtgag cactatgctg aaaaggtgc gaaggtgggc     540
gtccgagtga atccgggagt ggggtcggga ggcttctccg cgagtaccac tggattcagt     600
aaaactaatg tcggcggacc gagcagttcg ttcgggattt ggcacgaact cgtcaccgat     660
ggaaccgtcc cagatatcgt ggaaaggtac ggtttggaag tggaacgtat tcatacacat     720
attggatcag gtagtgatcc ggagatttgg cagcaagttg ccaccaaatc cttgtccttt     780
tgcaaggtgt ttcccaccgt caaaaccatg aatcttggtg cggctacaa ggtgggacgc     840
aacaagggcg aagttacgac agatttgcag aaaatcggga agcctgtggc ggatgccttt     900
aaaaagttcg cggaaaagga aggccgggaa ttgcaaatgg aaattgagcc cggaacttat     960
ctcgtggcca tggctggagc actcgtctcc aaggtccaag acaaggttca caccaccgga    1020
gagaatagcc acaccttctt gaagcttgat gccggcatga cggacgtctt cgccccgagc    1080
ttgtatggtg ccgtgcatcc tattacgatt ctgcccgggt cgggaaattc tgccgacgtt    1140
ggcgatgaaa ccgaatctgt agtggtggtt ggacattgtt gtgaatcagg gacctcatg    1200
actccggccc cgggtgagcc ggaacaacta gcggaacaag aacttcgtgc ggcagcggta    1260
ggtgatattc tagtgatgga tggctctggg gcgtactgct ccggcatgtc gacgaagaac    1320
tacaacagct ttcccgaagc accagaagtg ttggtggaca aggcaggcaa ggcacacttg    1380
atccgtaaac gacaaaccct gagtcaaatt tacgagaacg aaatctccgt agaaggcgtg    1440
ttttaa                                                               1446
```

<210> SEQ ID NO 7
<211> LENGTH: 484
<212> TYPE: PRT
<213> ORGANISM: Thalassiosira pseudonana

<400> SEQUENCE: 7

```
Met Lys Val Ser Ser Leu Ala Ile Val Thr Ala Leu Phe Ala Thr Ser
1               5                   10                  15

Thr Asn Ala Phe Ser Pro Ile Gln Pro His Ser Thr Thr Pro Ile Ile
            20                  25                  30

Thr Thr Ser Gln Leu His Ala Thr Pro Pro Ser Gln Ser Asn Phe Leu
        35                  40                  45

Thr Pro Glu Leu Ala Thr Thr Cys Ile Ala Thr Ala Gln Gly Thr Pro
    50                  55                  60
```

-continued

```
Leu Tyr Ala Tyr Ser Leu Ser Gln Leu Ala Ala Ala Thr Ala Thr
 65                  70                  75                  80

Leu Ala Phe Pro Asn Ala Phe Gly Leu Thr Val Arg Tyr Ala Met Lys
                 85                  90                  95

Ala Cys Pro Asn Gly Ser Ile Leu Lys Tyr Phe Leu Ser Arg Gly Ile
            100                 105                 110

Cys Ile Asp Ala Ser Ser Gly Tyr Glu Val Arg Arg Ala Met Ser Met
            115                 120                 125

Gly Val Pro Ala Glu Lys Ile Ser Leu Ser Ser Gln Glu Leu Pro Ala
130                 135                 140

Asp Phe Asp Glu Leu Ile Gly Leu Gly Val Lys Ile Asn Ala Cys Ser
145                 150                 155                 160

Val Ser Gln Leu Glu Arg Ile Gly Lys Ala Phe Pro Asn Thr Ser Gln
                165                 170                 175

Lys Val Gly Ile Arg Ile Asn Pro Gly Val Gly Ser Gly Gly Phe Ser
            180                 185                 190

Ser Ser Thr Thr Gly Phe Ser Lys Thr Asn Val Gly Gly Pro Ser Ser
            195                 200                 205

Ser Phe Gly Ile Trp His Glu Leu Val Thr Asp Gly Thr Val Pro Asp
210                 215                 220

Ile Val Thr Lys Tyr Gly Leu Glu Val Glu Arg Ile His Thr His Ile
225                 230                 235                 240

Gly Ser Gly Ser Asp Pro Ala Ile Trp Gln Ser Val Ala Thr Arg Ser
                245                 250                 255

Leu Ser Phe Cys Lys Leu Trp Asp Thr Ile Thr Thr Leu Asn Leu Gly
            260                 265                 270

Gly Gly Tyr Lys Val Gly Arg Asn Pro Gly Glu Lys Thr Thr Asp Leu
            275                 280                 285

Asn Glu Ile Gly Ala Pro Val Ala Asp Ala Phe Arg Asp Phe Ala Lys
290                 295                 300

Glu Thr Gly Arg Glu Leu Gln Met Glu Ile Glu Pro Gly Thr Tyr Leu
305                 310                 315                 320

Val Ala Asn Ala Gly Ala Leu Val Thr Thr Ile Gln Asp Lys Val Ser
                325                 330                 335

Thr Lys Ser Ala Ser Ser Asp Glu Gly His Ile Tyr Leu Lys Met Asp
            340                 345                 350

Ala Gly Met Thr Asp Val Leu Arg Pro Ser Leu Tyr Gly Ala Ile His
            355                 360                 365

Pro Ile Thr Ile Leu Pro Ala Ser Gly Lys Ser Ser Asp Ile Gly Thr
370                 375                 380

Ala Thr Glu Ser Val Val Val Gly His Cys Cys Glu Ser Gly Asp
385                 390                 395                 400

Leu Met Thr Pro Lys Pro Gly Glu Pro Glu Ala Leu Glu Glu Arg Val
                405                 410                 415

Leu Arg Thr Ala Glu Ile Gly Asp Ile Ala Val Met Asp Gly Ser Gly
            420                 425                 430

Ala Tyr Cys Ala Gly Met Ser Thr Lys Asn Tyr Asn Ser Phe Pro Glu
            435                 440                 445

Ala Pro Glu Val Leu Val Asp Leu Glu Gly Lys Val His Leu Ile Arg
450                 455                 460

Lys Arg Gln Ser Leu Gln Gln Ile Tyr Glu Asn Glu Cys Asp Val Pro
465                 470                 475                 480
```

Ser Gly Leu Phe

<210> SEQ ID NO 8
<211> LENGTH: 1455
<212> TYPE: DNA
<213> ORGANISM: Thalassiosira pseudonana

<400> SEQUENCE: 8

```
atgaaggtct ccagcctcgc catcgtaacg gccctattcg cgacctccac caatgccttc      60
tctccgatcc agccacacag caccacaccc atcatcacca cctctcaact ccacgccacg     120
cccccctccc aatccaactt cctcaccccc gaactagcca ccacctgcat cgccaccgcc     180
caaggcacgc ccctctacgc ctactccctc tcccaactag ccgccgccgc cacagccacc     240
ctcgccttcc ccaacgcatt cggtcttact gtacgatatg ccatgaaggc gtgtcccaat     300
ggaagtattt tgaagtactt tttgagtagg gggatttgta tcgatgcgag ttccgggtat     360
gaagtgagga gagcaatgag tatgggtgtt ccggccgaga agattagttt gagttcgcag     420
gagttgccgg cggattttga tgagttgatt ggtttggggg tcaagattaa tgcttgctcc     480
gtatcccaac tcgaacgcat cggcaaagcc ttccccaaca cctctcaaaa ggtaggcatc     540
cgcatcaacc ccggcgtagg atccggtgga ttctcctcct ccacaaccgg cttttccaaa     600
accaacgtcg gcggtccttc ctcctccttt ggtatctggc acgaactcgt taccgatgga     660
accgtacctg acattgtaac caagtatgga ttggaggtgg agaggattca cacccacatc     720
ggttcggggt cggatcctgc catttggcaa tcggttgcta ctcgctcttt gtcattctgt     780
aaactttggg atacaatcac aacattgaac ctcgggggag ggtacaaggt gggaagaaac     840
ccgggagaga aaaccactga cttgaatgag attgggcccc ctgttgccga tgcgtttagg     900
gactttgcaa aggagacggg gagggagttg cagatggaga tcgagccggg cacgtatttg     960
gttgcgaatg ctggagctct cgtgacgacg attcaggata aggtatcgac caaatcggca    1020
tcctccgacg aaggacacat ttacctcaaa atggatgctg gtatgacgga tgtccttcgt    1080
ccttccctct acggagccat tcatccaatc acaatcctcc ccgcatctgg aaagtcatct    1140
gacattggta ccgctaccga aagtgtcgtc gttgtaggac attgttgtga atctggagat    1200
ctcatgacac ccaaacctgg tgagcccgag gcattggaag aacgtgttct ccgtactgcc    1260
gagattggtg atattgccgt gatggatgga agtggagctt actgtgctgg aatgtcgact    1320
aagaattaca atagtttccc cgaggcgccg gaggtgttgg ttgatttgga aggaaaggtt    1380
catttgataa ggaagaggca gagtttgcag cagatttacg agaatgagtg tgatgttccc    1440
agtggtctct tttga                                                     1455
```

ENGINEERED MICROALGAE WITH ENHANCED LIPID PRODUCTION

RELATED APPLICATION

This application claims benefit under 35 U.S.C. § 119(e) of U.S. Provisional Patent Application No. 61/422,462, filed on Dec. 13, 2010.

SEQUENCE LISTING

The instant application contains a Sequence Listing which has been submitted electronically in ASCII format and is hereby incorporated by reference in its entirety. Said ASCII copy, created on Jan. 24, 2014, is named CVA-002.01_SL.txt and is 35,456 bytes in size.

BACKGROUND

Because of their high lipid and fatty acid content, microalgae, including diatoms, are regarded as a potentially useful source of neutral lipids for use in biodiesel fuel production. Theoretical calculations suggest that an annual oil production of greater than 200 barrels of algal oil per hectare of land may be achievable through mass culture of microalgae such as diatoms, which is 100-fold greater than that of soybeans, a major feedstock currently being used for biodiesel in the USA (Hu et al. *The Plant Journal*, 54:621-639 (2008)).

Under optimal growth conditions, diatoms and other microalgae synthesize fatty acids primarily for esterification into glycerol-based membrane lipids, which constitute about 5-20% of their dry cell weight. However, under unfavorable environmental conditions, such as during nitrogen deprivation, many algae shift their lipid profile towards the formation and accumulation of neutral lipids, principally in the form of triacylglycerol. Under such unfavorable growth conditions, the total lipid composition of certain microalgae can increase to above 50% of the algae's dry cell weight.

However, in addition to increasing lipid production, culture of microalgae under nutrient deprivation conditions also results in the halt of algal cell division. As a result, the increased lipid content of nutrient starved algae does not lead to an overall increase in lipid productivity. In fact, total rates of lipid production are typically lower under periods of nutrient starvation because higher cellular levels of lipid are offset by crashes in cell division. Thus, using existing technologies, it is possible either to culture microalgae under conditions that promote a high growth rate, or to culture microalgae under conditions that promote an elevated cellular TAG content, but it is not possible to do both simultaneously (Sheehan et al., 1998. A look back at the US Department of Energy's Aquatic Species Program-biodiesal from algae. National Renewable Energy Laboratory, Golden, Colo.; and Yu et al., *Journal of Applied Phycology*, 21:669-681 (2009)).

The development of microalgae cable of maintaining a lipid-rich phenotype under culture conditions that permit cell division would greatly enhance the economic viability of microalgae, including diatoms, as a source of biofuel precursors. Thus, there is a great need for engineered microalgae with enhanced lipid production during exponential growth.

SUMMARY

In one aspect, the invention features microalgae that have been engineered to assimilate carbon at a higher rate than nitrogen, thereby producing more lipid than wild-type microalgae during the exponential phase of cellular growth. In certain embodiments, the engineered microalgae is a diatom, such as *Phaeodactylum triconutum* or *Thalassiosira pseudonana*.

In certain embodiments, the microalgae has been engineered to produces more of a protein that facilitates carbon assimilation or a more active version of a protein that facilitates carbon assimilation. In certain embodiments the protein is selected from the group consisting of a pyr-decarboxylase, rubsico, beta CA or the chloroplast $HCO_3$ transporter.

In another embodiment, the microalgae has been engineered to produce less of a protein that facilitates nitrogen assimilation or a less active version of a protein that facilitates nitrogen assimilation. In certain embodiments, the protein that facilitates nitrogen assimilation is selected from the group consisting of nitrate reductase, nitrate transporter, NADPH nitrate reductase, ferredoxin nitrate reductase or glutamine synthetase II. In certain embodiments the engineered microalgae include a nucleic acid encoding an RNAi molecule that is an inhibitor of the expression of the protein that facilitates nitrogen assimilation. In another embodiment, the engineered microalgae includes a gene encoding a nitrogen assimilation protein that contains a mutation that reduces the expression or activity of the protein.

In another aspect, the invention features methods for producing lipids from microalgae. In one embodiment, the method comprises the steps of: a) growing a culture of the engineered microalgae for a sufficient period of time and under appropriate conditions to produce lipid during exponential growth of the microalgae culture; and b) harvesting lipids from the microalgae culture. In certain embodiments, the microalgae culture may be a biofilm.

In yet another aspect, the invention features expression vectors, which are comprised of a nucleic acid sequence encoding a protein that facilitates carbon assimilation operably linked to a transcription control element.

The engineered microalgae described herein are useful, for example, for the production of biofuels. Other features and advantages will be apparent from the following detailed description and from the claims.

BRIEF DESCRIPTION OF THE DRAWINGS

FIG. 2 shows the amino acid sequence (A, SEQ ID NO: 1) and nucleic acid sequence (B, SEQ ID NO: 2) of *Phaeodactylum triconutum* nitrate reductase.

FIG. 3 shows the amino acid sequence (A, SEQ ID NO: 3) and nucleic acid sequence (B, SEQ ID NO: 4) of *Thalassiosira pseudonana* nitrate reductase.

FIG. 4 shows the amino acid sequence (A, SEQ ID NO: 5) and nucleic acid sequence (B, SEQ ID NO: 6) of *Phaeodactylum triconutum* pyr-decarboxylase.

FIG. 5 shows the amino acid sequence (A, SEQ ID NO: 7) and nucleic acid sequence (B, SEQ ID NO: 8) of *Thalassiosira pseudonana* pyr-decarboxylase.

FIG. 6A shows NO production in *P. tricornutum* cell extracts as monitored by direct measurement of spin trapped NO $(MGD)_2$-Fe(II)—NO in electron paramagnetic resonance spectra (EPR). Normalized NO production was calculated by finding the average peak-to-trough height for the three peaks in the EPR spectrum. Basal NO levels were measured without substrates in wild type (WT) and overexpressing NR *P. tricornutum* cell lines. FIGS. 6B and 6C show confocal images of cytosolic and peroxisome localization of *P. tricornutum* NR-N'YFP respectively. FIG. 6D shows an electron micrograph of unfixed *P. tricornutum* wild type cells. The peroxisome is denoted by the arrow. FIG. 6E shows immunogold localization of *P. tricornutum* NR-N'YFP localized to the peroxisome.

DETAILED DESCRIPTION

Figure 1:
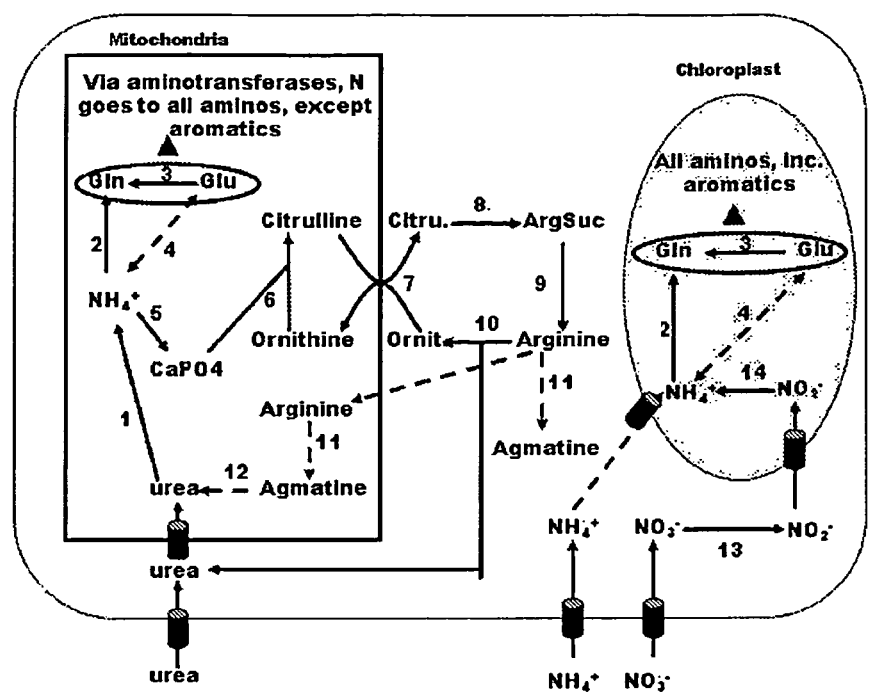
FIG. 1 shows pathways for nitrogen assimilation in *Phaeodactylum tricornutum*. Putative assimilation pathways for urea, $NH_4^+$, and $NO_3^-$ into amino acids are shown. $NH_4^+$, while shown as being assimilated in the plastid, may also be assimilated in the mitochondria. Numbers are for enzyme activity, not specific proteins: 1, Urease; 2, Glutamine synthase; 3, Glutamate synthase; 4, Glutamate dehydrogenase; 5, Carbamoyl phosphate synthase III; 6, Ornithine transcarbomylase; 7, Citrin; 8, Arginosuccinate synthase; 9, Arginosuccinate lyase; 10, Arginase; 11, Arginine decarboxylase; 12, Agmatinase; 13, Nitrate reducatase; and 14, Nitrite reductase. Dashed lines indicate putative pathways. Carbon containing metabolites are not shown.

Described herein are engineered microalgae that accumulate large amounts of lipids while still maintaining exponential growth. The microalgae have been engineered so that the amount of carbon assimilated is increased relative to wildtype, the amount of nitrogen assimilated is decreased relative to wildtype or a combination of both. These microalgae produce high levels of lipid during exponential cell growth. Such microalgae are useful, for example, for the production of lipids that can serve as biofuel precursors.

1. Definitions

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

As used herein the term "algae" represents a large, heterogeneous group of primitive photosynthetic organisms which occur throughout all types of aquatic habitats and moist terrestrial environments. The term "algae" includes, for example, diatoms (bacillariophytes), green algae (chlorophytes), blue-green algae (cyanophytes), golden-brown algae (chrysophytes), haptophytes, freshwater algae, saltwater algae, *Amphipleura, Amphora, Chaetoceros, Cyclotella, Cymbella, Fragilaria, Hantzschia, Navicula, Nitzschia, Phaeodactylum, Thalassiosira Ankistrodesmus, Botryococcus, Chlorella, Chlorococcum, Dunaliella, Monoraphidium, Oocystis, Scenedesmus, Nanochloropsis, Tetraselmis, Chlorella, Dunaliella, Oscillatoria, Synechococcus, Boekelovia, Isochysis* and *Pleurochysis*.

As used herein, the term "carbon assimilation" refers to the process by which microalgae concentrate $CO_2$ in chloroplast and the subsequent incorporation of carbon into biomass. Proteins that facilitate carbon assimilation include, but are not limited to, pyr-decarboxylase (e.g. GI:219122853, GI:223993801), Rubsico (e.g., GI:118411023, GI:118411104), Beta CA (e.g., GI:219109680) and Chloroplast $HCO_3$ transporter (e.g., GI:219118294, GI:219111471, GI:223994025).

As used herein, the term "diatom" refers to unicellular microalgae that are encased within a silica cell wall. Diatoms include both centric diatoms (e.g., *Thalassiosira pseudonana* and pinnate diatoms (e.g., *Phaeodactylum triconutum*).

As used herein, a nucleic acid sequence is "exogenous" to a cell if it had been artificially introduced into the cell or a parent of the cell. The exogenous nucleic acid may be from a different species or from the same species relative to the cell to which it was introduced. In the case where the nucleic acid is from the same species of the cell to which it was introduced, the introduced nucleic acid occupies a different location in the genome of the cell relative to the endogenous copy of the nucleic acid or is operably linked to different nucleic acids than the endogenous gene. The exogenous nucleic acid may be present in more than one copy in the cell. The exogenous nucleic acid may be maintained in a cell as an insertion into the genome or as an episomal molecule.

An "expression vector" is a vector which is capable of promoting transcription of a nucleic acid incorporated therein. Typically, the nucleic acid to be expressed is "operably linked" to a transcription control element, such as a promoter and/or an enhancer, and is therefore subject to transcription regulatory control by the transcription control element.

The term "gene" is used broadly to refer to any nucleic acid associated with a biological function. The term "gene" applies to a specific genomic sequence, as well as to a cDNA or an mRNA encoded by that genomic sequence.

The term "introduced" when referring to a heterologous or isolated nucleic acid refers to the incorporation of a nucleic acid into a eukaryotic or prokaryotic cell. The term includes such methods as "infection," "transfection," "transformation" and "transduction."

As used herein, the term "isolated" refers to the state in which substances (e.g., polynucleotides) are free or substantially free of material with which they are naturally associated such as other polypeptides or polynucleotides with which they are found in their natural environment or the environment in which they are prepared (e.g., cell culture).

As used herein, "lipids" are a class of molecules that are soluble in nonpolar solvents (such as ether and chloroform) and are relatively or completely insoluble in water. Lipid molecules consist predominantly of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids).

As used herein, the term "microalgae" includes all forms of microscopic, aquatic algae including, for example, phytoplankton and diatoms.

As used herein, the term "nitrogen assimilation" refers to the process by which microalgae reduce $NO_3^-$ to $NO_2^-$ and the subsequent incorporation of reduced nitrogen into biomass. Proteins that facilitate nitrogen assimilation include, but are not limited to, nitrate reductase (e.g., GI:21912672, GI:224010906), nitrate transporter (e.g., GI:219115383, GI:223998258), NADPH Nitrate Reductase (e.g., GI:219120092, GI:223995983), Ferredoxin Nitrate Reductase (e.g., GI:219119472, GI:223999185), Nitrate Transporter (e.g., GI:219120485, GI:223997254) and Glutamine Synthetase II (e.g., GI:219123807, GI:224012585).

As used herein, the terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers of analogs of naturally occurring nucleotides having the essential nature of natural nucleotides in that they hybridize to single-stranded nucleic acids in a manner similar to naturally occurring nucleotides (e.g., peptide nucleic acids).

As used herein, "operable linkage" refers to a functional linkage between two nucleic acid sequences, such as a transcription control element (e.g., a promoter) and the linked transcribed sequence. For example, a promoter is in operable linkage with a gene if it can mediate transcription of the gene.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that may or may not be able to replicate autonomously or integrate into a chromosome of a host cell.

2. Inhibition of Nitrogen Assimilation

Nitrogen assimilation in microalgae, including diatoms, is the process by which $NO_3^-$ is reduced to $NO_2^-$ and subsequently incorporated into cellular biomass. Microalgae, like other photosynthetic eukaryotes, reduce $NO_3^-$ to $NO_2^-$ using an assimilatory nitrate reductase enzyme (NR) NR catalyzed $NO_3^-$ reduction appears to be the rate-limiting process in nitrogen acquisition (Campbell, *Annu. Rev. Plant Physiol. Plant Mol.* 50:277-303 (1999)).

A simplified diagram of the nitrogen assimilation pathways in the diatom *Phaeodactylum tricornutum* is provided in FIG. 1, including putative assimilation pathways for urea, $NH_4^+$, and $NO_3^-$ into amino acids. In the case of urea, the mitochondrial location of urease indicates that the resulting ammonia is assimilated by the mitochondria GS-GOGAT or urea cycle. $NO_3^-$ derived ammonia is assimilated in the plastid, which is where nitrite reducatase is located. $NH_4^+$, while shown in FIG. 1 as being assimilated in the plastid, might also be assimilated in the mitochondria.

In one aspect, the instant invention relates to engineered microalgae, including engineered diatoms that do not assimilate as much nitrogen as wild-type (i.e. the corresponding microalgae, which has not been engineered). The reduction in the rate of nitrogen assimilation can be by any amount. In certain embodiments, the rate of nitrogen assimilation is reduced by at least 5%, 10%, 15%, 20%, 25%, 30%, 40%, 50%, 60%, 70% 80% or 90% relative to wild-type.

In some embodiments, the reduction in nitrogen assimilation can be achieved through the inhibition of the expression or activity of a protein that facilitates nitrogen assimilation. Inhibition of the expression or activity of a protein that facilitates nitrogen assimilation can be, but does not have to be, complete. For example, in certain embodiments, the expression or activity of the protein that facilitates nitrogen assimilation is reduced by at least 5%, 10%, 15%, 20%, 25%, 30%, 40%, 50%, 60%, 70% 80% or 90%. In certain embodiments, the activity or expression of the protein that facilitates nitrogen assimilation is not completely inhibited. Thus in some embodiments, nitrogen assimilation is inhibited by no more than 20%, 25%, 30%, 40%, 50%, 60%, 70% 80%, 90% or 95%.

Any protein that facilitates nitrogen assimilation can be inhibited in the engineered microalgae of the instant invention. In certain embodiments, the inhibited protein is nitrate reductase, which is a protein that catalyzes the rate limiting step in nitrogen assimilation. The nucleic acid sequence that encodes *Phaeodactylum triconutum* nitrate reductase is provided in SEQ ID NO: 2 and FIG. 2, while the nucleic acid sequence that encodes *Thalassiosira pseudonana* nitrate reductase is provided in SEQ ID NO: 4 and FIG. 3.

In some embodiments the inhibited protein is a facilitator of nitrogen assimilation other than nitrate reductase. For example, in certain embodiments, the inhibited protein that facilitates nitrogen assimilation is selected from a group consisting of nitrate reductase (e.g., GI:21912672, GI:224010906), Nitrate Transporter (e.g., GI:219115383, GI:223998258), NADPH Nitrate Reductase (e.g., GI:219120092, GI:223995983), Ferredoxin Nitrate Reductase (e.g., GI:219119472, GI:223999185), Nitrate Transporter (e.g., GI:219120485, GI:223997254) and Glutamine Synthetase II (e.g., GI:219123807, GI:224012585).

The expression or activity of proteins that facilitate nitrogen assimilation can be inhibited using any technique known in the art. For example, in certain embodiments, the expression of a protein that facilitates nitrogen assimilation is inhibited by a nucleic acid inhibitor, such as an RNA interference (RNAi) molecule or an antisense molecule. Techniques that employ nucleic acid inhibitors, such as RNAi and antisense inhibition, can be used in microalgae, including in diatoms, to inhibit expression of any protein of interest (De Riso et al., *Nucleic Acids Research* 37:e96 (2009), incorporated by reference in its entirety). Such nucleic acid inhibitors can be directly contacted with a microalgae cell. Alternatively, expression vectors encoding such molecules may be contacted with or introduced into a microalgae cell using any technique known in the art. Such vectors may, for example, incorporate into the microalgae genome or may remain episomal.

The nucleic acid inhibitor can be operably linked to any transcription control element that can induce transcription of the nucleic acid inhibitor in the microalgae to which it has been added. In certain embodiments, the transcription control element is a constitutive promoter, while in other embodiments the transcription control element is an inducible promoter. In certain embodiments, the transcription control element is selected from a group consisting of the 400 base pair region upstream of the fucoxanthin binding protein (FcpB. Siaut, M. et al. (2007) *Gene* 406:23-35; De Riso, V. et al., (2009) *Nucl. Acids Res* epub May 31, 2009); the promoter of the Fucoxanthin chlorophyll a/c protein (NCBI accession no. GI:219112237), the promoter of the *P. tricornutum* gene (GI:219127450), the promoter for diatom specific cell wall protein alpha frustulin 3 (GI:219117241), the promoter for polyubiquitin (GI:219118861), the promoter for the *P. tricornutum* gene (GI:219123984), and the promoter for *P. tricornutum* trypsin-like serine protease (GI:219116468) (Allen, A E et al., *Proc. Natl. Acad. Sci.* 105:10438-10443; Maheswari, U, et al., *Genome Biology* 11:R85).

In certain embodiments, the inhibitor is an RNAi molecule, for example, double-stranded (ds) RNA molecules of any length, siRNA molecules, shRNA molecules and amiRNA molecules. Such molecules are known in the art and the skilled artisan would be able to create oligonucleotide inhibitors of proteins that facilitate nitrogen assimilation using routine methods.

RNAi is the process through which dsRNA molecules inhibit the expression of mRNA to which the dsRNA has sequence homology. In plants, this process is also known as post-transcriptional gene silencing. Inhibition of mRNA expression can occur through a number of mechanisms, including epigenetic inhibition of the transcription of the mRNA molecule, targeted post-transcriptional degradation of the mRNA molecule, or inhibition of translation of the mRNA molecule. Because RNAi inhibition is primarily dependant on sequence homology between the dsRNA molecule and the mRNA target, RNAi molecules can be routinely designed to inhibit any mRNA target.

In certain embodiments, long dsRNA molecules are used to inhibit expression of a protein that facilitates nitrogen assimilation. Such dsRNA molecules may comprise at least 30, 40, 50, 60, 70, 80, 90, 100, 150, 200 or 250 nucleotides of the sequence that is homologous to the mRNA sequence that encodes the protein that facilitates nitrogen assimilation. Notably, the sequence of the long dsRNA molecule need not be identical to the mRNA sequence it inhibits. Thus, in certain embodiments the long dsRNA molecule is at least 70%, 75%, 80%, 85%, 90%, 95%, 96%, 97%, 98% or 99% identical to the mRNA that encodes a protein that facilitate nitrogen assimilation.

In certain embodiments, shorter RNAi molecules, such as small interfering RNA (siRNA) molecules, short hairpin (shRNA) molecules and artificial micro RNA (amiRNA) molecules, are used to inhibit expression of a protein that facilitates nitrogen assimilation. Such molecules typically have sequences that comprise at least 15, 19, 21, 22, or 23 nucleotides that are homologous to a target sequence. Like the long dsRNA molecules, the sequences of the shorter RNAi molecules do not have to be perfectly identical to the target. Thus, in certain embodiments, the sequence of the short RNAi molecule is at least 70%, 75%, 80%, 85%, 90% or 95% identical to the sequence of the mRNA that encodes a protein that facilitates nitrogen assimilation.

In certain embodiments, antisense oligonucleotides are used to interfere with expression of a protein that facilitates nitrogen assimilation. Typically an antisense molecule comprises at least 15, 17, 19, or 21 nucleotides of the complement of the mRNA sequence that encodes the protein that facilitates nitrogen assimilation. However, longer antisense RNA molecules can also be used. Thus, in certain embodiments, antisense RNA molecules can be up to 50, 100, 200, 300, 400, 500 or more nucleotides in length. Furthermore, the sequence of antisense molecules need not be perfectly complementary to the mRNA sequence it inhibits. Thus, in certain embodiments, the antisense RNA molecule is at least 70%, 75%, 80%, 85%, 90%, 95%, 96%, 97%, 98% or 99% complementary to the mRNA that encodes a protein that facilitate nitrogen assimilation.

In certain embodiments, the engineered microalgae of the instant invention contain a mutation that inhibits the expression or activity of a protein that facilitates nitrogen assimilation. In certain embodiments, the mutation is in the gene that encodes the protein that facilitates nitrogen assimilation. In some embodiments, the mutation is in an endogenous transcription control element operably linked to a gene encoding a protein that facilitates nitrogen assimilation. The mutation can: (i) completely eliminate the activity or expression of the protein, (e.g., through a complete knock-out mutation), (ii) reduce the activity of the protein (e.g. through a point mutation to the protein-coding region of the protein), or (iii) reduce the expression of the protein (e.g., through a mutation to the transcription control element operably linked to the protein).

Mutations that inhibit the expression or production of a nitrogen assimilating protein can be introduced into a microalgae using any method known in the art. Because of the small size and rapid growth of microalgae, a desired mutation can be generated through techniques such as random mutagenesis and screening. Certain microalgae, including the diatoms *Phaeodactylum triconutum* and *Thalassiosira pseudonana*, are particularly suitable for mutagenesis, because their genomes are relatively small and have been completely sequenced. Mutagenesis can be performed using methods known in the art, including radiation or chemically induced mutations. Screens for a desired mutation can be performed, for example, using whole genome oligonucleotide tilling arrays (see, e.g., Mock et al., *PNAS*, 5:1579-1584 (2008), incorporated by reference in its entirety), through direct sequencing of the gene of interest, by monitoring expression of the mRNA or protein of interest, or by phenotype screening for microalgae that produce high levels of lipid during exponential growth.

3. Enhancement of Carbon Assimilation

Carbon assimilation in microalgae, including diatoms, is the process by which $CO_2$ is concentrated in chloroplasts and subsequently incorporated into cellular biomass. In diatoms and other microalgae, much of carbon assimilation occurs in pyrenoids. The pyrenoid is a subcellular crystalline structure within the chloroplast of unicellular algae, but is absent in plants. This "suborganelle" contains mostly rubisco, fructose bisphopsphate aldloase (FBA) and a β-carbonic anhydrase (CA) and it is the location where photosynthetically driven carbon fixation occurs.

The existence of pyrenoids facilitates $CO_2$ concentrating mechanisms that are essential to carbon assimilation in microalgae. Due to the low affinity of rubisco for $CO_2$, interference from $O_2$, and the low concentrations of $CO_2$ in aquatic systems, microalgae must deliver large amounts of $CO_2$ to rubisco in order for carbon fixation to occur. This can be achieved either biophysically or biochemically. The biophysical approach involves bicarbonate uptake and then delivery to the pyrenoid with transporters, and subsequent conversion to $CO_2$ by a carbonic anhydrase that is located close to the active site of carbon fixation.

$CO_2$ may be biochemically concentrated by carboxylating an organic acid outside of the chloroplast, delivering to the chloroplast by a transporter and decarboxylating at the site of rubisco. Inhibitors of the anaplerotic carboxylase phosphoenolpyruvate carboxylase (PEPC) have been shown to reduce carbon fixation in certain microalgae, including *P. tricornutum*, indicating the presence of a biochemical $CO_2$ concentrating mechanism (McGinn and Morel, *Plant Physiology*, 146:300-309 (2008)). Pyrenoid-localized decarboxylase, ("pyr-decarboxylase"), a highly conserved protein present in all of the currently sequenced marine phytoplankton genomes, but not in cyanobacteria or plants, is involved in biochemical carbon fixation. The pyr-decarboxylase gene in *P. tricornautam* is shown in FIG. 4 and SEQ ID NOs: 5 and 6. The pyr-decarboxylase gene in *T. pseudonana* is shown in FIG. 5 and SEQ ID NOs: 7 and 8.

In another aspect, the instant invention relates to engineered microalgae, including engineered diatoms, that have an increased level of carbon assimilation. The increase in the rate of carbon assimilation can be by any amount. In certain embodiments, the rate of carbon assimilation is increased by at least 25%, 50%, 75%, 100% or 200%.

In some embodiments, the elevation in carbon assimilation can be achieved through an increase in the expression or activity of a protein that facilitates carbon assimilation. Increase in the expression or activity of a protein that facilitates carbon assimilation can be by any amount. For example, in certain embodiments, the expression or activity of the protein that facilitates carbon assimilation is increased by at least 25%, 50%, 75%, 100% or 200%.

The expression or activity of any protein that facilitates carbon assimilation can be increased in the engineered microalgae of the instant invention. In certain embodiments, the protein is pyr-decarboxylase. The nucleic acid sequence that encodes *Phaeodactylum triconutum* pyr-decarboxylase is provided in SEQ ID NO: 6 and FIG. 4, while the nucleic acid sequence that encodes *Thalassiosira pseudonana* pyr-decarboxylase is provided in SEQ ID NO: 8 and FIG. 5. In certain embodiments, the invention relates to an isolated nucleic acid molecule or vector that comprises a sequence encoding pyr-decarboxylase operably linked to a transcription control element.

In some embodiments the protein is a facilitator of carbon assimilation other than pyr-decarboxylase. For example, in certain embodiments, the protein that facilitates carbon assimilation is selected from a group consisting of pyr-decarboxylase (e.g. GI:219122853, GI:223993801), Rubsico (e.g., GI:118411023, GI:118411104), Beta CA (e.g., GI:219109680) and Chloroplast $HCO_3$ transporter (e.g., GI:219118294, GI:219111471, GI:223994025).

The expression or activity of proteins that facilitate carbon assimilation can be increased using any technique known in the art. For example, in certain embodiments, the expression of a protein that facilitates carbon assimilation is increased in microalgae through the introduction into the microalgae of a nucleic acid that encodes a protein that facilitates carbon assimilation operably linked to a transcription control element that drives transcription of the nucleic acid in the microalgae. For example, expression vectors encoding such molecules may be introduced into a microalgae cell using any technique known in the art. Such vectors may, for example, incorporate into the microalgae genome or may remain episomal. In other embodiments, the expression of an endogenous gene that encodes a protein that facilitates carbon assimilation is increased, for example, by operably linking it to an exogenous transcription control element.

Any transcription control element that drives expression of an operably linked nucleic acid in microalgae of interest can be used. In certain embodiments, the transcription control element is a constitutive promoter, while in other embodiments the transcription control element is an inducible promoter. In certain embodiments, the transcription control element is selected from a group consisting of is selected from a group consisting of the promoter of the 400 base pair region upstream of the fucoxanthin binding protein (FcpB. Siaut, M. et al. (2007) *Gene* 406:23-35; De Riso, V. et al., (2009) *Nucl. Acids Res* epub May 31, 2009); the promoter of the Fucoxanthin chlorophyll a/c protein (NCBI accession no. GI:219112237), the promoter of the *P. tricornutum* gene (GI:219127450), the promoter for diatom specific cell wall protein alpha frustulin 3 (GI:219117241), the promoter for polyubiquitin (GI:219118861), the promoter for the *P. tricornutum* gene (GI:219123984), and the promoter for *P. tricornutum* trypsin-like serine protease (GI: 219116468) (Allen, A E et al., *Proc. Natl. Acad. Sci.* 105:10438-10443; Maheswari, U, et al., *Genome Biology* 11:R85).

4. Engineered Microalgae

In certain embodiments, the instant invention relates to engineered microalgae with enhanced lipid expression during exponential growth. In some embodiments, the microalgae are engineered such that their rate of nitrogen assimilation is reduced relative to wild-type. In some embodiments, the microalgae are engineered such that their rate of carbon assimilation is increased relative to wild-type.

The microalgae to be engineered can be any species in which inhibition of nitrogen assimilation or elevation of carbon assimilation leads to enhanced lipid production during exponential growth. In certain embodiments the species of the engineered microalgae of the instant invention is selected from the group consisting of *Phaeodactylum tricornutum*, *Thalassiosira pseudonana*, *Dunaliella tertio-*

*lecta, Chlamydomonas reinhardtii, Volvox varteri, Aureococcos anophagefferens* and *Nanochloropsis* sp.

In certain embodiments, the engineered microalgae of the instant invention are a diatom. Diatoms are unicellular microalgae that are encased within a silica cell wall. Diatoms include both centric diatoms and pinnate diatoms. In some embodiments, the species of the microalgae is *Phaeodactylum triconutum* or *Thalassiosira pseudonana*. The genomes of *P. triconutum* and *T. pseudonana* have been completely sequenced and are publically available.

The engineered microalgae can be grown under any condition appropriate for their particular species. Exemplary growth conditions for microalgae can be found in, for example, U.S. Patent Application Publication Nos. 2009/0215140, 2009/0274736, 2010/0151339, 2010/0170144, 2010/0184197 and 2010/0261918. For example, if the engineered microalgae is a diatom, it can be grown as a batch culture under continuous fluorescent light at 18° C. in 0.2 μm filtered and autoclaved coastal seawater amended with f/2 nutrients using $NO_3^-$ as the sole nitrogen source, as described in Guillard, *Culture of Marine Invertebrate Animals*. Plenum Press, New York, pp. 29-60 (1978) and Allen et al., *J. Phycol.* 41:95-105 (2005), each of which is incorporated by reference in its entirety.

Certain microalgae, such as *P. triconutum*, are capable of being cultured as a biofilm. Methods of inducing microalgae growth as a biofilm are known in the art. For example, exemplary methods can be found in Stanley and Callow, *European Journal of Phycology* 42:191-197 (2007) and Vardi et al., *Current Biology* 18:895-899 (2008). The growth of microalgae in a biofilm can be useful because it facilitates the harvesting of lipids secreted into the growth media. Thus, in certain embodiments, the invention relates to the growth of the engineered microalgae of the invention in a biofilm.

5. Methods of Lipid Production

In certain embodiments, the instant invention relates to methods for producing lipids using the engineered microalgae of the instant invention. In certain embodiments, this method comprises the steps of: (1) growing a culture of the engineered microalgae for a sufficient period of time and under appropriate conditions such that lipid is produced during exponential growth and (2) harvesting lipids from the microalgae culture.

Engineered microalgae can be grown under condition, which are well known in the art including, but not limited to, those described herein. In certain embodiments, the engineered microalgae are grown under conditions in which they are not nutrient (e.g., nitrogen or silicon) deprived. In certain embodiments, the engineered microalgae are grown under conditions such that a nucleic acid encoding a RNAi molecule that inhibits expression of a protein that facilitates nitrogen assimilation is transcribed. In some embodiments, the engineered microalgae are grown under conditions such that a nucleic acid encoding a protein that facilitates carbon assimilation is transcribed.

Any of a variety of methods known in the art can be used for harvesting lipids from microalgae (See, for example, U.S. Patent Application Publication Nos. 2010/0151339, 2010/0170144, 2010/0184197 and 2010/0261918.

In certain embodiments, microalgae may be separated from the medium and various components, including lipids, may be extracted using any method known in the art. For example, microalgae may be partially separated from the medium using a standing whirlpool circulation, harvesting vortex and/or sipper tubes or other methods known in the art. Alternatively, industrial scale commercial centrifuges of large volume capacity may be used. Such centrifuges may be obtained from known commercial sources (e.g., Cimbria Sket or IBG Monforts, Germany; Alfa Laval A/S, Denmark). Centrifugation, sedimentation and/or filtering may also be of use to purify lipids from other microalgal components. Separation of microalgae from the aqueous medium may be facilitated by addition of flocculants, such as clay (e.g., particle size less than 2 microns), aluminum sulfate, FeCl3 at pH about pH 9-10, polyacrylamide or the like. In the presence of flocculants, microalgae may be separated by simple gravitational settling, or flotation, or may be more easily separated by centrifugation. Flocculant-based separation of microalgae is disclosed, for example, in U.S. Patent Application Publication No. 2002/0079270, incorporated herein by reference in its entirety.

In certain embodiments, microalgae may be disrupted to facilitate separation of lipids. Any method known for microalgae disruption may be utilized, such as ultrasonication, French press, osmotic shock, mechanical shear force, cold press, thermal shock, rotor-stator disruptors, valve-type processors, fixed geometry processors, nitrogen decompression or any other known method.

The invention now having been generally described will be more readily understood by reference to the following examples, which are included merely for purposes of illustration and are not intended to be limiting in any way.

EXAMPLES

Example 1: Generation of Engineered Microalgae Having Reduced Nitrogen Assimilation Both *P. triconutum* and *T. pseudonana* encode a single copy of nitrate reductase (NR), the enzyme that controls the rate-limiting step of nitrogen assimilation in all known eukaryotic marine algae (Allen et al., *J. Phycol.* 41:95-104 (2005)). Transgenic diatoms that expressed a NR-yellow fluorescence protein (YFP) N'-terminus fusion revealed that NR is localized in both the cytoplasm and the peroxisome. This localization was further verified using immuno-gold labeling transmission electron microscopy (TEM) (FIG. 6).

Figure 7:
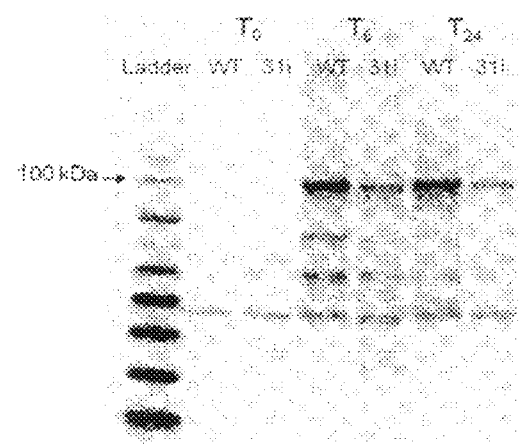
FIG. 7 shows an immunoblot analysis using primary antibody raised specifically on *P. tricornutum* NR. The *P. tricornutum* NR protein is predicted to be 890AA, MW 100.12 kDa. *P. tricornutum* cultures were grown on $NH_4^+$ ($T_0$), pelleted washed and resuspended in $NO_3^-$ and assayed for NR protein content at 6 and 24 hrs after resuspension in $NO_3^-$. Normalized 100 kDa band volumes are $T_6$ WT, 1.46 ug; $T_6$ 31i, 0.849; $T_{24}$ WT, 1.59 ug; $T_{24}$ 31i, 0.57.

To generate an engineered diatom having reduced nitrogen assimilation, vectors encoding an RNAi molecule that inhibited NR were developed. Using relative growth rates on nitrate and ammonium as a preliminary screen, several putative NR-RNAi lines were identified. These engineered diatoms exhibit reduced growth rates on nitrate relative to ammonium, over 50% reduced NR activity in crude protein extracts, and reductions by 40-60% in NR protein relative to wild type as determined through immunoblotting (FIG. 7). These engineered cell lines have been stable for over 18 months.

Figure 8:
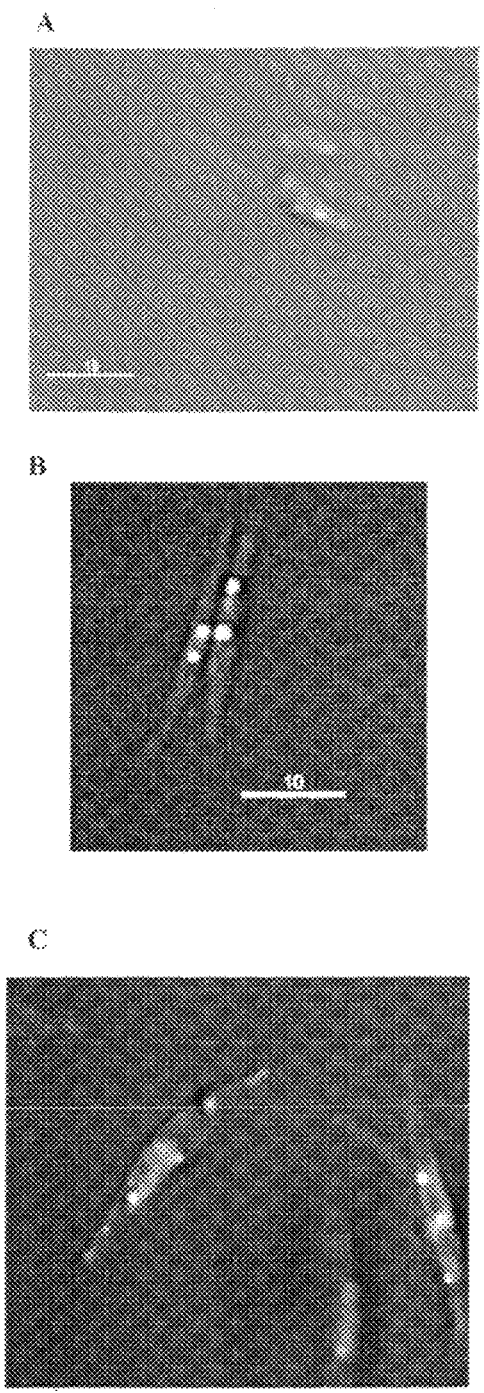
FIG. 8 shows images taken using CARS confocal micriscopy imaging specific for lipids performed on exponential- and stationary phase-wild type and NR RNAi line *P. tricornutum* cells. 8A is a representative image of a wild type exponential *P. tricornutum* cell. 8B is a representative image of a wild type stationary *P. tricornutum* cell. 8C is a representative image of a NR RNAi exponential *P. tricornutum* cell.

Example 2: Engineered Microalgae Having Reduced Nitrogen Assimilation Exhibit Enhanced Lipid Production During Exponential Growth Engineered diatoms having reduced nitrogen assimilation were generated as described above. Observations with light microscopy revealed the presence of numerous lipid droplets in the engineered diatom culture, even when the diatoms were experiencing exponential growth. Further light microscopy and epifluorescence experiments using LipidTox neutral green confirmed that these were lipid-rich droplets, which further confirmed using confocal microscopy was performed on a CARS (Coherent Anti-Stokes Raman Scattering) platform verified that these droplets are in fact composed of lipid (FIG. 8).

Figure 9:
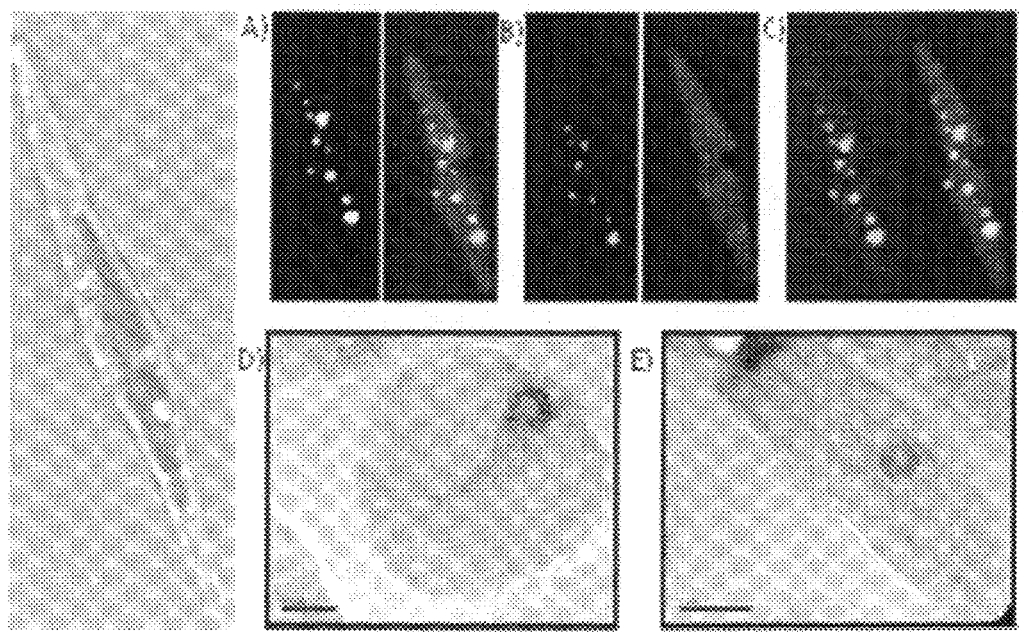
FIG. 9 shows chloroplast pyrenoid localization of *P. triconutum* overexpressing fluorescently tagged native Fructose Bisphosphate Aldolase (FBA) and β Carbonic Anydrase (CA). Confocal micrographs of 9A is C' YFP tagged FBA; 9B is C' CFP tagged β-CA; 9C is an overlay of C' YFP tagged FBA and C' CFP tagged β-CA; 9D and 9E are electron micrographs of immunogold localization of β-CA.

Notably, the exponentially growing engineered microalgae exhibit a similar lipid distribution to nitrogen-limited stationary phase wild type microalgae Example 3: Generation of Engineered Microalgae Having Increased Carbon Assimilation As described above, the pyrenoid is a subcellular crystalline structure within the chloroplast of microalgae but not plants. This "suborganelle" contains mostly rubisco, fructose bisphopsphate aldloase (FBA) and a-carbonic anhydrase (CA) and it is the location where photosynthetically driven carbon fixation occurs (FIG. 9).

Pyrenoid localization facilitates $CO_2$ concentrating mechanisms that are essential to microalgae. Because of the low affinity of rubisco for $CO_2$, interference from $O_2$, and the low concentrations of $CO_2$ in aquatic systems, microalgae must deliver large amounts of $CO_2$ to rubisco. This can be achieved biophysically or biochemically.

Figure 10:
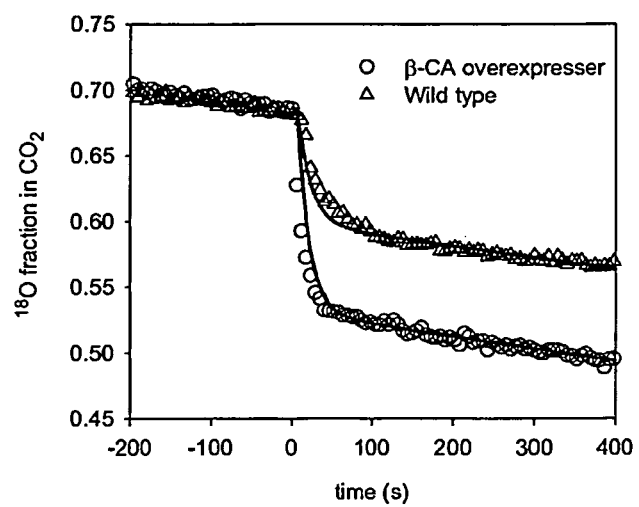
FIG. 10 shows an analysis of CA activity in a β-CA over-expression *P. tricornutum* cell line. In separate analyses, equivalent numbers of wild type or β-CA overexpressing *P. tricornutum* cells were added to the MIMS chamber (at t=0) which contained $^{18}O$ enriched inorganic carbon. $^{18}O$ in $CO_2$ is exchanged with $^{16}O$ from water by cycles of hydration/dehydration, a process catalyzed by CA once cells are added.

The biophysical approach involves bicarbonate uptake and then delivery to the pyrenoid with transporters, and subsequent conversion to $CO_2$ by a carbonic anhydrase that is located closely to the active site of carbon fixation. Using inlet membrane mass spectrometry (MIMS) we have found that overexpression of the pyrenoid localized CA in *P. tricornutum* results in increased delivery of bicarbonate and carbon fixation; these experiments provide evidence for a potential for a biophysical CCM (FIG. 10).

The biochemical approach involves carboxylation of an organic acid outside of the chloroplast, followed by delivery and decarboxylation at the site of rubisco. Inhibitors of the anaplerotic carboxylase phosphoenolpyruvate carboxylase (PEPC) have been shown to reduce carbon fixation in *P. tricornutum*, indicating that it plays a role in biochemical CCM.

Figure 11:
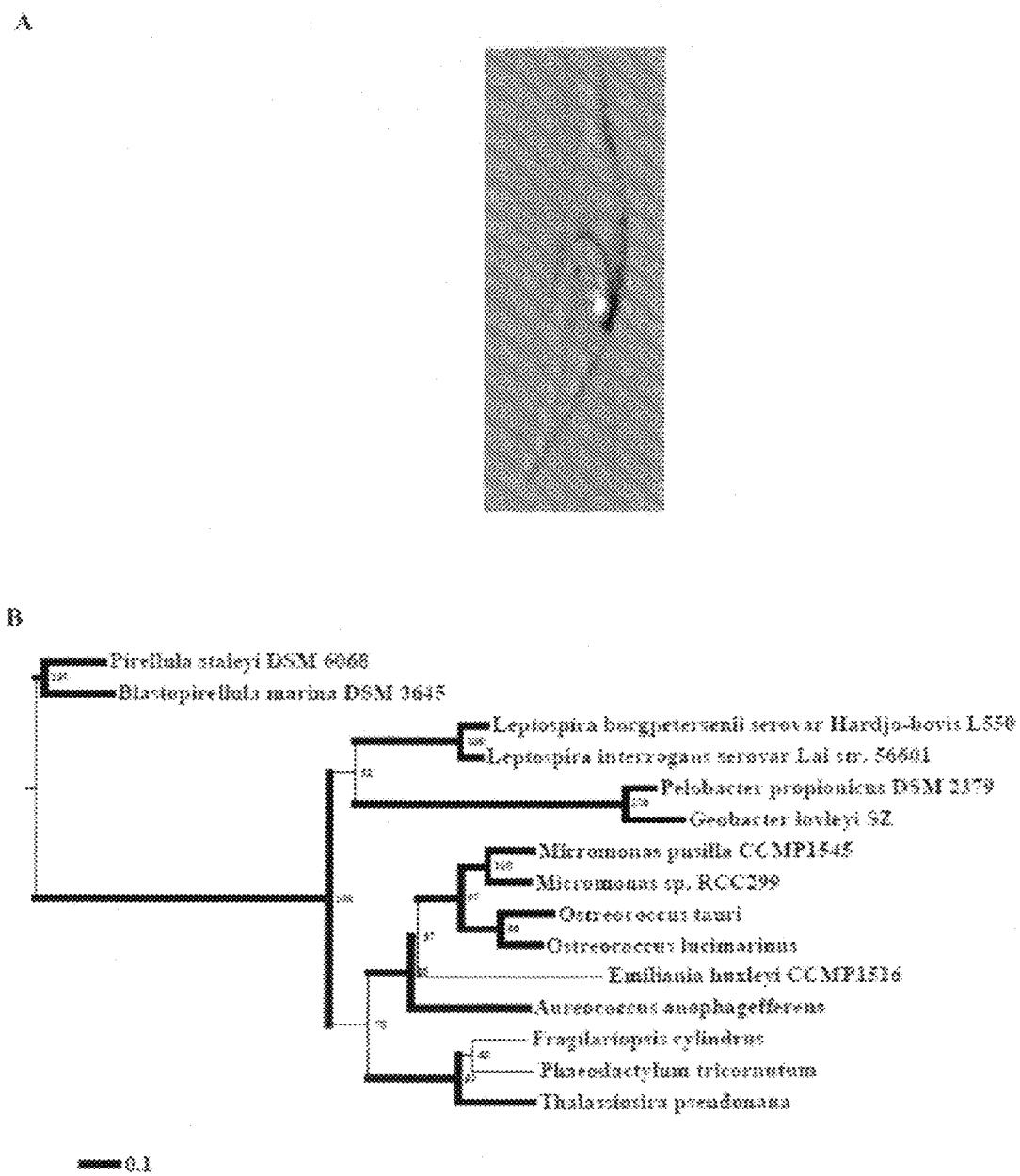
FIG. 11A shows a confocal micrograph of C' YFP tagged *P. tricornutum* protein 21592; a putative ornithine/arginine/diaminopimelate family decarboxylase. The autofluorescence in the center of the cell is the plastid. This location was recognized from previous experience to be consistent with pyrenoid localization.
FIG. 11B shows bootstrapped (100 replicates) maximum likelihood (ML) phylogenetic tree of an ornithine/arginine/diaminopimelate family decarboxylase proteins (*P. tricornutum* protein ID 21592) as inferred by the PROML program of PHYLIP 3.69, and midpoint rooted. The alignment (515 columns) was created by aligning the decarboxylase proteins with MUSCLE 3.8.31 and removing columns that contained more than 20% gaps.

To generate an engineered microalgae with enhanced carbon assimilation, a putative ornithine/arginine/diaminopimelate family decarboxylase (protein id 21592) was fused with C' YFP and overexpressed. Confocal microscopy revealed that the decarboxylase localized to the pyrenoid (FIG. 11a). Based on its localization, the decarboxylase was called "pyr-decarboxylase". Manual examination of the decarboxylase amino acid sequence revealed a canonical TAAFAP amino acid motif used for targeting and import to complex multi-membrane diatom plastids (Vugrinec et al., *Journal of Cell Biology* 88:81-81 (2009)). The localization of the *P. tricornutum* pyr-decarboxylase (PtPyrDecarboxylase) indicates that it may be the missing link for a biochemical CCM in *P. tricornutum*. Furthermore, pyr-decarboxylase is conserved in all marine phytoplankton genomes sequenced to date (FIG. 11b), but absent in other major green lineages such as cyanobacteria and plants.

Figure 12:
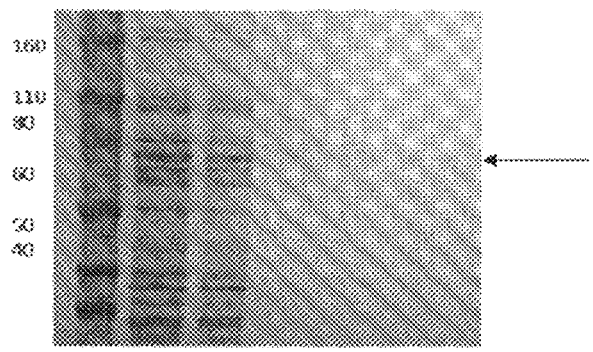
FIG. 12 shows SDS PAGE gel of the PtPyrDecar-C' GST fusion product and purification: lane 1) Molecular marker, 2) *E. coli* cell lysate, 3) Flow through containing most of the whole proteins, 4-6) Fractions 1-3 collected after wash and elution of GST protein

PtPyrDecarboxylase was fused with a C'terminus glutathione S-transferase and cloned into an *Escherichia coli* expression vector with an L-arabinose induction system. After induction, the PtPyrDecarboxylase-C'GST was purified using glutathione affinity chromatography (FIG. 12).

Example 4: Engineered Microalgae Having Increased Carbon Assimilation Exhibit Enhanced Lipid Production During Exponential Growth

Figure 13:
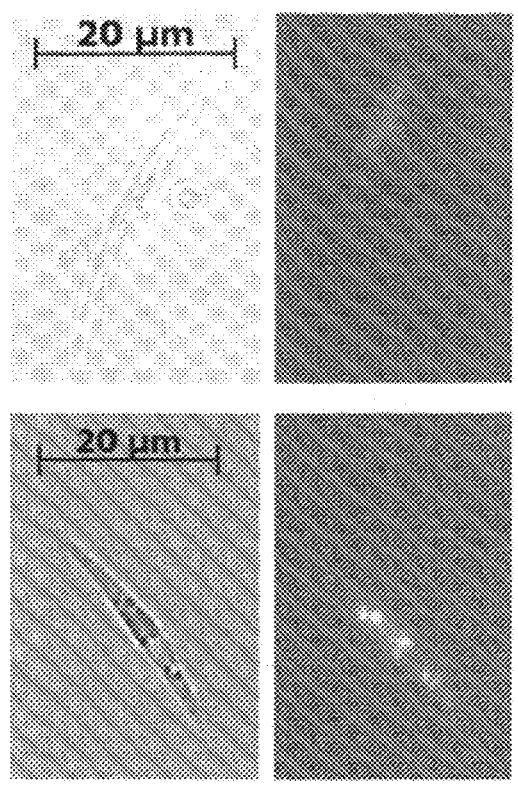
FIG. 13 shows LipidTox green stains of (top) exponential phase-wild type cells and (bottom) exponential phase PtPyrDecar-over expression cell lines.

*P. tricornutum* overexpresssing PtPyrDecarboxylase-YFP exhibit wild-type growth rates in typical media. As with the NR-RNAi engineered microalgae, the PtPyrDecarboxylase-YFP microalgae contain a large number of visible lipid droplets while in exponential growth. Preliminary epifluorescence studies with LipidTox neutral green confirm that droplets are packed with lipids, and the cells are also more lipid rich than exponentially growing wild type cells (FIG. 13).

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

We claim:

1. An engineered diatom that produces lipid during exponential growth, wherein the diatom has been stably engineered with an exogenous nucleic acid to
   reduce or completely eliminate the expression level or activity of a protein that facilitates nitrogen assimilation, said protein is glutamine synthetase,
   relative to the wild-type diatom.

2. The engineered microalgae diatom of claim 1, which is *Phaeodactylum triconutum* or *Thalassiosira pseudonana*.

3. The engineered diatom of claim 1, wherein the nucleic acid and the transcription control element are both exogenous.

4. The engineered diatom of claim 3, wherein the transcription control element is the fucoxanthin binding protein promoter.

5. The engineered diatom of claim 1, wherein the nucleic acid is an RNAi molecule that is an inhibitor of the expression of the protein that facilitates nitrogen assimilation.

6. The engineered diatom of claim 5, wherein the nucleic acid is operably linked to a transcription control element.

7. The engineered diatom of claim 6, wherein the transcription control element is the fucoxanthin binding protein promoter.

8. The engineered diatom of claim 1, wherein the nucleic acid encodes a nitrogen assimilation protein that contains a mutation that reduces or completely eliminates the expression or activity of the protein.

9. A method of producing lipids from a diatom comprising:
   a) growing a culture of the engineered diatom of claim 1 for a sufficient period of time and under appropriate conditions such that lipid production is enhanced during exponential growth; and b) harvesting lipids from the diatom culture.

10. The method of claim 9, wherein the diatom is grown in a biofilm.

* * * * *